United States Patent
Finkelstein et al.

(10) Patent No.: US 6,749,850 B1
(45) Date of Patent: Jun. 15, 2004

(54) METHODS, COMPOSITIONS AND KITS FOR PROMOTING RECOVERY FROM DAMAGE TO THE CENTRAL NERVOUS SYSTEM

(75) Inventors: Seth P. Finkelstein, Needham, MA (US); Evan Y. Snyder, Jamaica Plain, MA (US)

(73) Assignees: The General Hospital Corporation, Boston, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/642,277

(22) Filed: Aug. 18, 2000

Related U.S. Application Data
(60) Provisional application No. 60/149,561, filed on Aug. 18, 1999.

(51) Int. Cl.$^7$ .................... A61K 35/14; A61K 38/08
(52) U.S. Cl. .................... 424/93.7; 424/93.1; 514/12
(58) Field of Search .................... 424/93.7, 198.1; 514/12

(56) References Cited

U.S. PATENT DOCUMENTS

| | | | |
|---|---|---|---|
| 5,175,103 A | 12/1992 | Lee et al. | 435/172.3 |
| 5,270,191 A | 12/1993 | McKay et al. | 435/172.3 |
| 5,733,871 A | 3/1998 | Alps et al. | 514/12 |
| 5,750,376 A | 5/1998 | Weiss et al. | 435/69.52 |
| 5,753,506 A | 5/1998 | Johe | 435/377 |
| 5,817,773 A | 10/1998 | Wilson et al. | 530/399 |
| 5,840,580 A | 11/1998 | Terstappen et al. | 435/372 |
| 5,914,108 A | 6/1999 | Tsukamoto et al. | 424/93.7 |
| 5,958,767 A | 9/1999 | Snyder et al. | 435/368 |
| 5,968,829 A | 10/1999 | Carpenter | 435/467 |

FOREIGN PATENT DOCUMENTS

| | | | |
|---|---|---|---|
| EP | 86117257.5 | * | 6/1987 |
| EP | 89101162.9 | * | 8/1989 |
| FR | 2 642 086 | * | 7/1990 |
| WO | WO 94/03199 | | 2/1994 |
| WO | WO 95/24469 | | 9/1995 |
| WO | WO 96/15224 | | 5/1996 |
| WO | WO 97/34618 | | 9/1997 |
| WO | WO 00/00588 | | 1/2000 |
| WO | WO 00 69448 | | 11/2000 |
| WO | WO 00/71715 | * | 11/2000 |

OTHER PUBLICATIONS

Barker et al., Neural transplantation therapies for parkinson's and huntington's diseases, 2001, DDT, vol. 6, pp. 575–582.*

Kmiec, Investigators have been searching for ways to add corrective genes to cells harboring defective genes . . . , 1999, American Scientist, vol. 87, pp. 240–247.*

Daughaday et al., Insulin–like growth factors I and II. Peptide, messenger ribonucleic acid and gene structures, serum, and tissue concentrations, 1989, Endocrine Reviews, vol. 10, pp. 68–91.*

Dinsmore, J. et al., "Embryonic Stem Cells Differentiated In Vitro As A Novel Source Of Cells For Transplantation", Cell Transplantation USA 5(2): 131–143 (1996).

Kennedy, T.E. et al., "Netrins Are Diffusible Chemotropic Factors For commissural Axons In The Embryonic Spinal Cord", Cell USA 78: 425–435 (Aug. 1994).

Marciniak, A. et al., "Neural Stem Cells, In Combination With Basic Fibro–Blast Growth Factor (bFGF), May Represent A Treatment For Stroke", Experimental Neurology 164(2): 444 (Aug. 2000).

Strömberg, M. et al, "Chronic Implants Of Chromaffin Tissue Into The Dopamine–Denervated Striatum. Effects of NGF On Graft Survival, Fiber Growth And Rotational Behavior", Exp Brain Res 60: 335–349 (1985).

International Search Report, PCT Pub. No. WO 01/12236, filed Aug. 18, 2000.

Aebischer, P. et al., "Transplantation of Polymer Encapsulated Neurotransmitter Secreting Cells: Effect of the Encapsulation Technique", Journal of Biomechanical Engineering 113: 178–183 (May 1991).

Andersson, Candace et al., "Transplantation of Cultured Type 1 Astrocyte Cell Suspensions into Young, Adult and Aged Rat cortex: Cell Migration and Survival", Int. J. Devl. Neuroscience 11(5): 555–568 (1993).

Andsberg, Gunner et al., "Amelioration of Ischaemia–Induced Neuronal Death in the Rat Striatum by NGF–Secreting Neural Stem Cells", European Journal of Neuroscience 10: 2026–2036 (1998).

Bavetta, Seb et al., "The Effects of FK506 on Dorsal Column Axons Following Spinal Cord Injury in Adult Rats: Neuroprotection and Local Regeneration", Experimental Neurology 158: 382–393 (1999).

Bhatia, Mickie et al., "A Newly Discovered Class of Human Hemetopoietic Cells with SCID–Repopulating Activity", Nature Medicine 4(9): 1038–1045 (Sep. 1998).

Chen, Jun; MD, et al., "Intracerebral Transplantation of Bone Marrow with BDNF after MCAo in Rat", Neuropharamacology 39: 711–716 (2000).

Lopez–Coviella, Ignacio et al., "Induction and Maintenance of the Neuronal Cholinergic Phenotype in the Central Nervous System by BMP–9", Science 289: 313–316 (Jul. 14, 2000).

(List continued on next page.)

*Primary Examiner*—Anne-Marie Falk
*Assistant Examiner*—Daniel M. Sullivan
(74) *Attorney, Agent, or Firm*—Foley Hoag LLP

(57) ABSTRACT

The present application relates to methods, kits and compositions for improving a subject's recovery from CNS injury. In certain aspects, methods of the invention comprise administering to a subject cells and a neural stimulant. Recovery may be manifest by improvements in sensorimotor or cognitive abilities, e.g., improved limb movement and control or improved speech capability. In certain embodiments, subject methods can be used as part of a treatment for damage resulting from ischemia, hypoxia or trauma.

7 Claims, 6 Drawing Sheets

OTHER PUBLICATIONS

Cramer, Steven C., MD et al., "A Functional MRI Study of Subjects Recovered from Hemiparetic Stroke", Stroke 28: 2518–2527 (199&).

Eglitis, Martin A. et al., "Hematopoietic Cells Differentiate into Both Microglia and Macroglia in the Brains of Adult Mice", Proc. Natl. Acad. Sci. USA 94: 4080–4085 (Apr. 1997).

Evans, M.J. et al., "Establishment in Cluture of Pluripotential Cells from Mouse Embryos", Nature 292: 154–156 (Jul. 9, 1981).

Fisher, Marc et al., "Delayed Treatment with Intravenous Basic Fibroblast Growth Factor Reduces Infarct Size Following Permanent Focal Cerebral Ischemia in Rats", Journal of Cerebral Blood Flow and Metabolism 15: 953–959 (1995).

Flax, Jonathan D. et al., "Engraftable Human Neural Stem Cells Respond to Developmental Cues, Replace Neurons, and Express Foreign Genes", Nature Biotechnology 16(11): 1033–1039 (Nov. 1998).

Gage, Fred H., "Survival and Differentiation of Adult Neuronal Progenitor Cells Transplanted to the Adult Brain", Proc. Natl. Acad. Sci. USA 92: 11879–11883 (Dec. 1995).

Griffith, Diana L. et al., "Three–Dimensional Structure of Recombinant Human Osteogenic Protein 1: Structural Paradigm for the Transforming Growth Factor β Superfamily", Proc. Natl. Acad. Sci. USA 93: 878–883 (Jan. 1996).

Jones, Theresa A. et al., "Use–Dependant Growth of Pyramidal Neurons after Neocortical Damage", Journal of Neuroscience 14(4): 2140–2152 (Apr. 1994).

Kawamata, Takakazu et al., "Intracisternal Antisense Oligonucleotide to Growth Associated Protein–43 Blocks the Recovery–Promoting Effects of Basic Fibroblast Growth Factor after Focal Stroke", Experimental Neurology 158: 89–96 (1999).

Kawamata, Takakazu et al., "Intracisternal Basic Fibroblast Growth Factor (bFGF) Enhances Behavioral Recovery Following Focal Cerebral Infarction in the Rat", Journal of Cerebral Blood Flow and Metabolism 16: 542–547 (1996).

Kawamata, Takakazu et al., "Intracisternal Basic Fibroblast Growth Factor Enhances Functional Recovery and Up–Regulates the Expression of a Molecular Marker of Neuronal Sprouting Following Focal Cerebral Infarction", Proc. Natl. Acad. Sci. USA 94: 8179–8184 (Jul. 1997).

Kuhn, H. Georg et al., "Epidermal Growth Factor and Fibroblast Growth Factor–2 Have Different Effects on Neural Progenitors in the Adult Rat Brain", Journal of Neuroscience 17(15): 5820–5829 (Aug. 1, 1997).

Ling, Zao Dung et al., "Differentiation of Mesencephalic Progenitor Cells into Dopaminergic Neurons by Cytokines", Experimental Neurology 149: 411–423 (1998).

Lobsiger, Christian S. et al., "Platelet–Derived Growth Factor–BB Supports the Survival of Cultured Rat Schwann Cell Precursors in Synergy with Neurotrophin–3" GLIA 30: 290–300 (2000).

Martin, Gail R., "Isolation of a Pluripotent Cell Line from Early Mouse Embryos Cultured in Medium Conditioned by Teratocarcinoma Stem Cells", Proc. Natl. Acad. Sci. USA 78(12): 7634–7638 (Dec. 1981).

Mehler, Mark F. et al., "Cytokine Regulation of Neuronal Differentiation of Hippocampal Progenitor Cells", Nature 362: 62–64 (Mar. 4, 1993).

Miraglia, Sheri et al., "A Novel Five–Transmembrane Hematopoietic Stem Cell Antigen: Isolation, Characterization and Molecular Cloning", Blood 90(12): 5013–5021 (Dec. 15, 1997).

Park, Kook In et al., "Transplantation of Neural Progenitor and Stem Cells: Developmental Insights May Suggest New Therapies for Spinal Cord and Other CNS Dysfunction" Journal of Neurotrauma 16(8): 675–687 (1999).

Ray, Jasodhara et al., "A 10–Amino Acid Sequence of Fibroblast Growth Factor 2 is Sufficient for its Mitogenic Activity on Neural Progenitor Cells", Proc. Natl. Acad. Sci. USA 94: 7047–7052 (Jun. 1997).

Ren, JingMei, et al., "Time Window of Intracisternal Osteogenic Protein–I in Enhancing Functional Recovery after Stroke", Neuropharmacology 39: 860–865 (2000).

Snyder, Evan Y. et al., "Multipotent Neural Precursors can Differentiate Toward Replacement of Neurons Undergoing Targeted Apoptotic Degeneration in Adult Mouse Neocortex", Proc. Natl. Acad. Sci. USA 94: 11663–11668 (Oct. 1997).

Stroemer, R. Paul PhD et al., "Enhanced Neocortical Neural Sprouting, Synaptogenesis, and Behavioral Recovery with D–Amphetamine Therapy after Neocortical Infarction in Rats", Stroke 29: 2381–2395 (1998).

Tamura, A. et al., "Focal Cerebral Ischaemia in the Rat:1. Description of Technique and Early Neuropathological Consequences Following Middle Cerebral Artery Occlusion", Journal of Cerebral Blood Flow and Metabolism 1: 53–60 (1981).

Thomson, James A. et al., "Embryonic Stem Cell Lines Derived from Human Blastocysts", Science 282: 1145–1147 (Nov. 6, 1998).

Van Vactor, David et al., "Neural Development: The Semantics of Axon Guidance", Current Biology 9: R201–R204 (1999).

Villa, Ana et al., "Establishment and Properties of a Growth Factor–Dependant, Perpetual Neural Stem Cell Line from the Human CNS", Experimental Neurology 161: 67–84 (2000).

Withers, G. S. et al., "Bone Morphogenetic Protein–7 Enhances Dendritic Growth and Receptivity in Innervation in Cultured Hippocampal Neurons", European Journal of Neuroscience 12: 106–116 (2000).

Yrjanheikki, Juha et al., "Tetracyclines Inhibit Microglial Activation and are Neuroprotective in Global Brain Ischemia", Proc. Natl. Acad. Sci. USA 95: 15769–15774 (Dec. 1998).

* cited by examiner

Human bFGF amino acid sequences

22.5 kD form (Genbank GI: 482272; SEQ. ID. No. 1)

```
1   mgdrgrgral pggrlggrgr grapervggr grgrgtaapr aapaargsrp gpagtmaags
61  ittlpalped ggsgafppgh fkdpkrlyck nggfflrihp dgrvdgvrek sdphiklqlq
121 aeergvvsik gvcanrylam kedgrllask cvtdecfffe rlesnnynty rsrkytswyv
181 alkrtgqykl gsktgpgqka ilflpmsaks
```

114 amino acid form (Genbank GI: 8250666; SEQ. ID. No. 2)

```
1   lgdrgrgral pggrlggrgr grapervggr grgrgtaapr aapaargsrp gpagtmaags
61  ittlpalped ggsgafppgh fkdpkrlyck nggfflrihp dgrvdgvrek sdph
```

88 amino acid form (Genbank GI: 4261553; SEQ. ID. No. 3)

```
1   flrihpdgrv dgvreksdph iklqlqaeer gvvsikgvca nrylamkedg rllaskcvtd
61  ecffferles nnyntyrsrk ytswyval
```

Fig. 4

SEQUENCE LISTING

<160> NUMBER OF SEQ ID NOS: 4

<210> SEQ ID NO 1
<211> LENGTH: 210
<212> TYPE: PRT
<213> ORGANISM: Homo sapiens

<400> SEQUENCE: 1

```
Met Gly Asp Arg Gly Arg Gly Arg Ala Leu Pro Gly Gly Arg Leu Gly
  1               5                  10                  15

Gly Arg Gly Arg Gly Arg Ala Pro Glu Arg Val Gly Gly Arg Gly Arg
             20                  25                  30

Gly Arg Gly Thr Ala Ala Pro Arg Ala Ala Pro Ala Ala Arg Gly Ser
         35                  40                  45

Arg Pro Gly Pro Ala Gly Thr Met Ala Ala Gly Ser Ile Thr Thr Leu
     50                  55                  60

Pro Ala Leu Pro Glu Asp Gly Gly Ser Gly Ala Phe Pro Pro Gly His
 65                  70                  75                  80

Phe Lys Asp Pro Lys Arg Leu Tyr Cys Lys Asn Gly Gly Phe Phe Leu
                 85                  90                  95

Arg Ile His Pro Asp Gly Arg Val Asp Gly Val Arg Glu Lys Ser Asp
                100                 105                 110

Pro His Ile Lys Leu Gln Leu Gln Ala Glu Glu Arg Gly Val Val Ser
            115                 120                 125

Ile Lys Gly Val Cys Ala Asn Arg Tyr Leu Ala Met Lys Glu Asp Gly
        130                 135                 140

Arg Leu Leu Ala Ser Lys Cys Val Thr Asp Glu Cys Phe Phe Phe Glu
145                 150                 155                 160

Arg Leu Glu Ser Asn Asn Tyr Asn Thr Tyr Arg Ser Arg Lys Tyr Thr
                165                 170                 175

Ser Trp Tyr Val Ala Leu Lys Arg Thr Gly Gln Tyr Lys Leu Gly Ser
            180                 185                 190

Lys Thr Gly Pro Gly Gln Lys Ala Ile Leu Phe Leu Pro Met Ser Ala
        195                 200                 205

Lys Ser
    210
```

<210> SEQ ID NO 2
<211> LENGTH: 114
<212> TYPE: PRT
<213> ORGANISM: Homo sapiens

<400> SEQUENCE: 2

```
Leu Gly Asp Arg Gly Arg Gly Arg Ala Leu Pro Gly Gly Arg Leu Gly
  1               5                  10                  15

Gly Arg Gly Arg Gly Arg Ala Pro Glu Arg Val Gly Gly Arg Gly Arg
             20                  25                  30

Gly Arg Gly Thr Ala Ala Pro Arg Ala Ala Pro Ala Ala Arg Gly Ser
         35                  40                  45
```

-continued

```
Arg Pro Gly Pro Ala Gly Thr Met Ala Ala Gly Ser Ile Thr Thr Leu
     50                  55                  60

Pro Ala Leu Pro Glu Asp Gly Gly Ser Gly Ala Phe Pro Pro Gly His
 65              70                  75                  80

Phe Lys Asp Pro Lys Arg Leu Tyr Cys Lys Asn Gly Gly Phe Phe Leu
             85                  90                  95

Arg Ile His Pro Asp Gly Arg Val Asp Gly Val Arg Glu Lys Ser Asp
                100                 105                 110

Pro His

<210> SEQ ID NO 3
<211> LENGTH: 88
<212> TYPE: PRT
<213> ORGANISM: Homo sapiens

<400> SEQUENCE: 3

Phe Leu Arg Ile His Pro Asp Gly Arg Val Asp Gly Val Arg Glu Lys
 1               5                  10                  15

Ser Asp Pro His Ile Lys Leu Gln Leu Gln Ala Glu Glu Arg Gly Val
             20                  25                  30

Val Ser Ile Lys Gly Val Cys Ala Asn Arg Tyr Leu Ala Met Lys Glu
         35                  40                  45

Asp Gly Arg Leu Leu Ala Ser Lys Cys Val Thr Asp Glu Cys Phe Phe
     50                  55                  60

Phe Glu Arg Leu Glu Ser Asn Asn Tyr Asn Thr Tyr Arg Ser Arg Lys
 65                  70                  75                  80

Tyr Thr Ser Trp Tyr Val Ala Leu
                 85

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:
      Illustrative tetrapeptide sequence

<400> SEQUENCE: 4

Arg Gly Asp Ser
 1
```

METHODS, COMPOSITIONS AND KITS FOR PROMOTING RECOVERY FROM DAMAGE TO THE CENTRAL NERVOUS SYSTEM

This application claims priority to U.S. Provisional Application No. 60/149,561, filed Aug. 18, 1999, incorporated herein by reference in its entirety.

1. BACKGROUND

The central nervous system (CNS) is particularly vulnerable to insults that result in cell death or damage in part because cells of the CNS have a limited capacity for repair. As a result, disorders of the CNS often result in debilitating and largely irreversible degradation of a patient's cognitive and sensorimotor functions. Conditions that result in nerve cell death and damage range from degenerative disorders, such as Alzheimer's disease, to ischemic episodes, such as stroke, to trauma.

Injury to the central nervous system (CNS) is an important cause of death and disability worldwide. For example, stroke is the third leading cause of death and disability in the U.S., with an estimated incidence of 700,000 cases annually (Furie et al. (1998) "Cerebrovascular Disease" in *The Atlas of Clinical Neurology*, R. N. Rosenberg, Ed. Current Medicine: Philadelphia). Two-thirds of stroke patients survive the first year following stroke, for an average of seven years, leading to more than 4.8 million stroke survivors currently in the U.S. Stroke costs the U.S. economy in excess of $30 billion per year in terms of medical costs and lost wages.

After several hours, little can be done to prevent the direct damage to the CNS caused by CNS disorders. For example, stroke treatments must typically be administered within six hours of onset. Depending on where the injury occurs in the brain, patients may be paralyzed on one side, may lose the ability to speak or see, and may have difficulty walking, among other symptoms. Gradual recovery of these functions is common, although recovery may be incomplete, and depends on the size and location of injury, among other factors.

Since damaged brain tissue does not regenerate, recovery must come from the remaining intact brain, which reorganizes itself, or rewires, in order to compensate for some of the function lost by the damage. Indeed, studies in animals and humans provide ample evidence of such reorganization of brain function following stroke. In particular, remaining neurons in both the damaged hemisphere and in the opposite intact hemisphere grow new processes (both axons and dendrites) and form new connections (synapses), which most likely contribute to recovery (Kawamata et al. (1997) *Proc. Natl. Acad. Sci. USA*, 94: 8179–8184; Jones et al. (1994) *J. Neurosci.*, 14: 2140–2152; Stroemer et al. (1998) *Stroke*, 29: 2381–2395; Cramer et al. (1997) *Stroke*, 28: 2518–2527).

As an example, stroke treatment has focused on limiting the extent of damage within the first few hours. Stroke is generally due to a blockage of an artery leading to the brain, resulting in the death of brain cells supplied by that artery. Current treatments for stroke have centered on treatments to prevent arterial blockages (control of blood pressure, lipids, heart disease, etc.), and treatments to prevent brain damage once the blockage has occurred. These latter treatments include "thrombolytic agents" ("clot busters" such as tPA) to break up arterial clots, and "neuroprotective agents," designed to protect brain tissue at risk for stroke. Such thrombolytic and neuroprotective agents must be administered within hours after the onset of stroke in order to be effective.

Currently there are only a few available methods of promoting recovery in patients after cell death and injury has already occurred. Methods of treating stroke after the initial phase of damage are mechanistically different from methods used in the first few hours. Treatments to promote recovery typically focus on encouraging neuronal growth and rewiring.

Direct application of neurotrophic growth factors to the brain can enhance spontaneous functional recovery occurring in animal models of stroke (Kawamata et al. (1997) *Proc. Natl. Acad. Sci. USA*, 94: 8179–8184; Kawamata et al. (1996) *J. Cereb. Blood Flow Metab.*, 16: 542–547; Kawamata et al. (1999) *Exp. Neurol.* 158: 89–96; Alps et al., U.S. Pat. No. 5,733,871, Fisher et al. (1995) *J. Cereb. Blood Flow Metab.*, 15: 953–959; Jiang et al. (1996) *J. Neurol. Sci.*, 139: 173–179). For example, basic fibroblast growth factor (bFGF) is a protein that supports survival and axonal outgrowth from neurons. When bFGF is administered starting a day or more after stroke, animals recover more quickly and to a greater extent on tests of sensorimotor function of the impaired limbs (opposite to the side of the stroke). This recovery is not due to a decrease in magnitude of the original brain damage. Instead, data suggests that this enhancement of recovery may be due to enhancement of new neuronal sprouting and synapse formation in the intact remaining brain tissue. Such remodeling appears to occur in both the damaged and undamaged hemispheres. Other mechanisms of recovery may include stimulation of endogenous neural stem cells within the brain that then differentiate into neurons, replacing to some extent neurons lost by stroke.

Another potential approach to a treatment for stroke recovery includes the use of neural stem cells. These are pluripotential cells already present in the developing and mature mammalian brain that, given the appropriate stimulation, can differentiate into brain neurons and/or glial cells. Several investigators have been successful in separating and cloning out such neural stem cell lines from both the murine and human brain (Snyder et al. (1997) *Proc. Natl. Acad. Sci. USA*, 94: 11663–11668; Gage et al. (1995) *Proc. Natl. Acad. Sci. USA*, 92: 11879–11883; Kuhn et al. (1997) *J. Neurosci.*, 17: 5820–5829; McKay et al., U.S. Pat. No. 5,270,191; Johe, K., U.S. Pat. No. 5,753,506; Carpenter, M., U.S. Pat. No. 5,968,829; Weiss et al., U.S. Pat. No. 5,750, 376). When such stem cells are reintroduced into the developing or mature brain, they can divide, migrate, grow processes, and assume neural phenotypes, including the expression of neurotrarsmitters and growth factors normally elaborated by neurons. Thus, use of neural stem cells may be advantageous for stroke recovery in at least two ways: (1) by the stem cells partially repopulating dead areas and re-establishing neural connections lost by stroke, and (2) by secretion of important neurotrarsmitters and growth factors required by the brain to rewire after stroke. Efforts to promote recovery from brain injury in animals using neural stem cells have been described (Park et al. (1999) *J. Neurotrauma* 16: 675–687; Park et al. (1995) *Soc. Neurosci. Abs.* 21: 2027; Stroemer et al. (1999) *Soc. Neuroscience Abs.* 25:1310). Efforts using a line of teratocarcinoma-derived cells have also been described in animals (Borlongan et al. (1993) *Int. J. Devl. Neuroscience* 11: 555–568) and humans (Kokaia et al. (1998) *Eur. J. Neurosci.*, 10: 2026–36).

Methods currently available for promoting recovery from CNS damage allow only partial recovery of neurological functions. In patients suffering from debilitating neurological deficits, incremental improvements in function may have a significant effect on quality of life. Given the large number of affected patients and the limitations of current methods, there is an urgent need for additional and improved methods to promote recovery from damage to the nervous system. The modes of treatment presented herein promote a greater degree of recovery from CNS damage than is currently available with other known treatment methods.

2. SUMMARY OF THE INVENTION

One aspect of the present application relates to methods for improving a subject's recovery from CNS injury or damage. In one aspect, the invention comprises administering to a subject cells, preferably stem cells, and a neural stimulant in sufficient amounts to improve the subject's sensorimotor or cognitive abilities, e.g., improved limb movement and control or improved speech capability.

In another aspect, the invention provides kits for the treatment of CNS damage. In certain embodiments, kits of the invention comprise stem cells and a neural stimulant. In other embodiments, the kits of the invention comprise a neural stimulant and a device for obtaining a stem cell-containing sample from a subject. In preferred embodiments, the kits comprise a polypeptide growth factor, and more preferably a polypeptide at least 30% identical but most preferably at least 40%, 50%, 60%, 70%, 80%, 90%, 95%, 98%, 99% or 100% identica of the polypeptides of SEQ. ID. Nos. 1–3.

In a further aspect, the invention provides pharmaceutical preparations comprising stem cells, a neural stimulant and one or more pharmaceutically acceptable reagents.

In preferred embodiments, stem cells for use in the invention are cells capable of giving rise to brain cells, eg. neurons, oligodendroglia or astroglia. In particularly preferred embodiments, stem cells are neural stem cells, hematopoietic stem cells, teratocarcinoma-derived cells or embryonic stem cells. In other preferred embodiments, stem cells are obtained from the subject, and optionally cultured or enriched in vitro prior to administration.

In other embodiments, stem cells of the invention may be induced to proliferate in vitro by transfection with a gene encoding one or more proliferation promoting factors, such as vmyc, SV40 T antigen, polyoma virus large T antigen, the neu oncogene or the ras oncogene. In preferred embodiments, the gene is strongly expressed in vitro, promoting proliferation, and poorly expressed after the cell has entered the central nervous system, such that the cell does not proliferate rapidly in vivo.

In a further embodiment, the neural stimulant is a polypeptide growth factor. Preferred polypeptide growth factors comprise a polypeptide that is chosen from among the following polypeptide families: fibroblast growth factor family members, neurotrophin family members, insulin-like growth factor family, ciliary neurotrophic growth factor family members; EGF family members, TGFβ family members, leukemia inhibitory factor (LIF); oncostatin M, interleukin-11; interleukin-6; members of the platelet-derived growth factor family, and VEGF family members. It is contemplated that, in certain embodiments, combinations of factors may be used. Preferred polypeptides comprise a polypeptide with a sequence that is at least 30%, 40%, 50%, 60%, 70%, 80%, 90%, 95%, 98%, 99% or 100% percent identical to an amino a sequence shown in any of SEQ ID Nos. 1–3.

In still other embodiments, the neural stimulant is a modulator of neutrarsmitter activity (eg. an agonist or antagonist). In preferred embodiments, the neural stimulant is an antidepressant, such as Prozac, an amphetamine, Ritalin, a tricyclic antidepressant such as Elavil, or combinations thereof. In another embodiment, the neural stimulant is a promoter of neuronal differentiation such as retinoic acid. In yet another embodiment, the neural stimulant is a so-called guidance molecule such as a netrin, a semaphorin, a neuropilin or an ephrin. In yet an additional embodiment, the neural stimulant may be transcranial magnetic stimulation.

In another aspect, the invention comprises conjoint administration of cells with a bioactive compound that is not a neural stimulant. Preferred bioactive compounds include immunosuppressants such as immunophilins (eg. cyclosporin, FK506, and thalidomide) and antibiotics, such as tetracycline.

A range of techniques for administering the cells and neural stimulants of the invention are contemplated. Cells and neural stimulants do not need to be administered in the same way or at the same time, but they are preferably administered such that their effects overlap. In preferred embodiments, administration is carried out at least 6, 10, 12 or 24 hours after the injury has occurred.

3. BRIEF DESCRIPTION OF THE FIGURES

FIGS. 1A–D represents data from Example 1 in graphical form.

FIGS. 2A–D represents in data from Example 2 in graphical form.

Figure 1A:
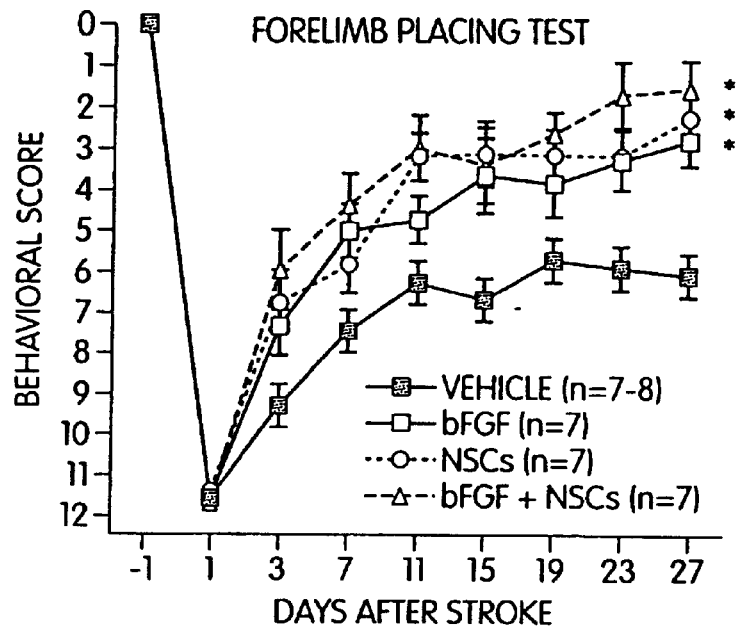
FIG. 1B is a graph that illustrates the results of hindlimb placing tests in a rat stroke model.
FIG. 1C is a graph that illustrates the results of bodyswing tests in a rat stroke model.
FIG. 1D is a graph showing the results of spontaneous limb use tests in a rat stroke model.
Figure 1B:
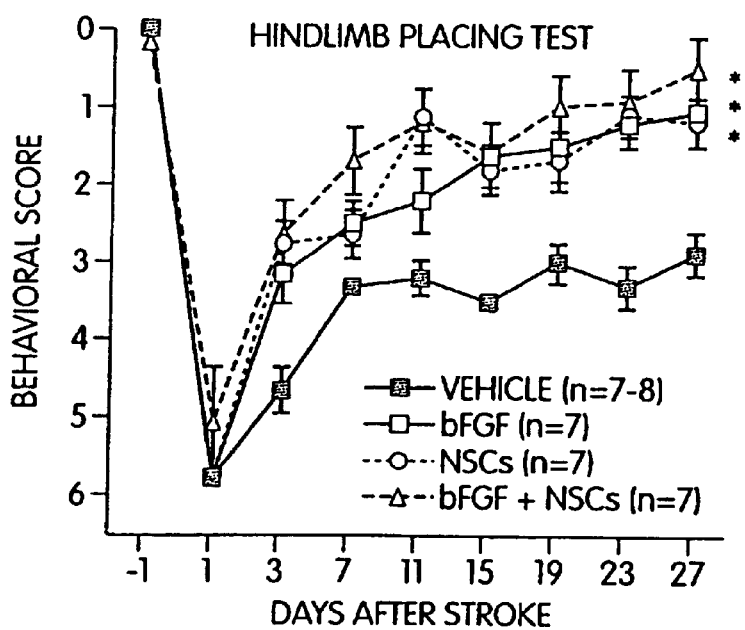
Figure 1C:
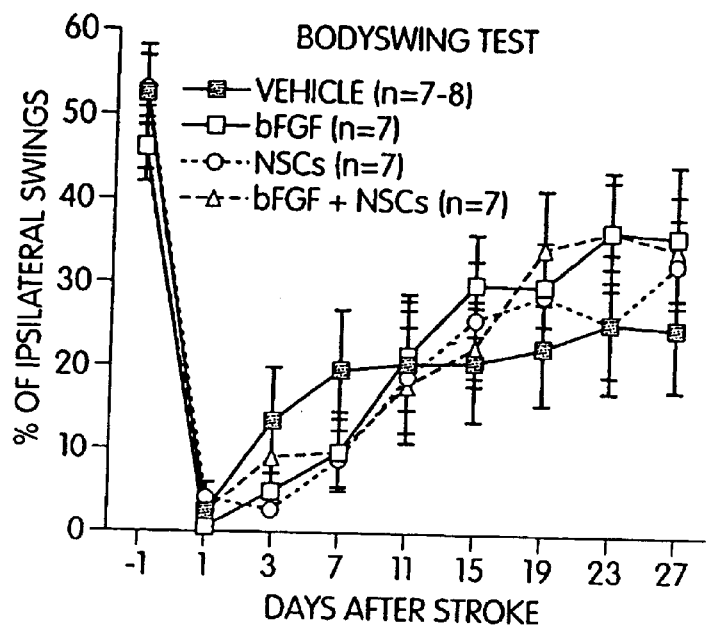
Figure 1D:
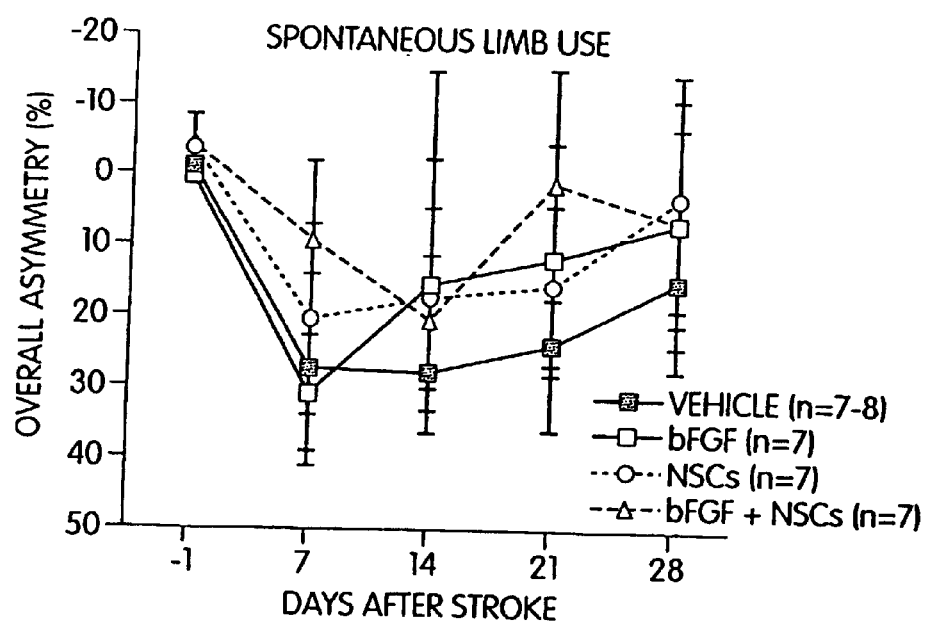
Figure 2A:
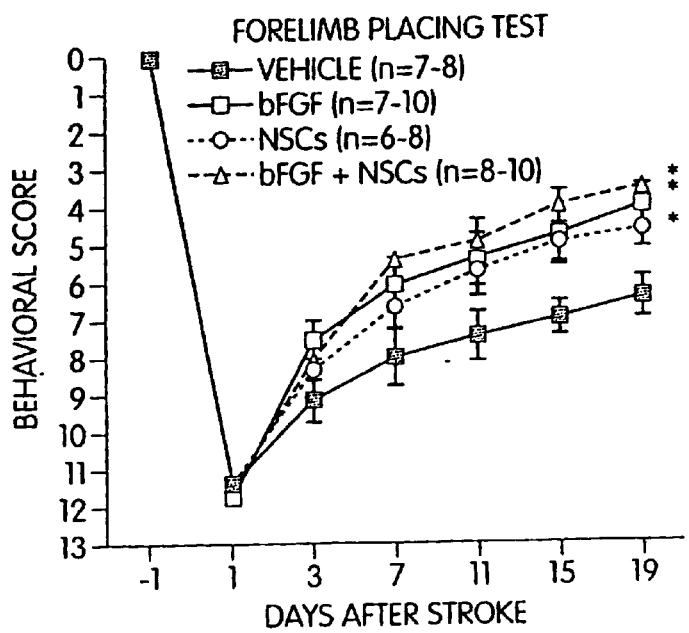
Figure 2B:
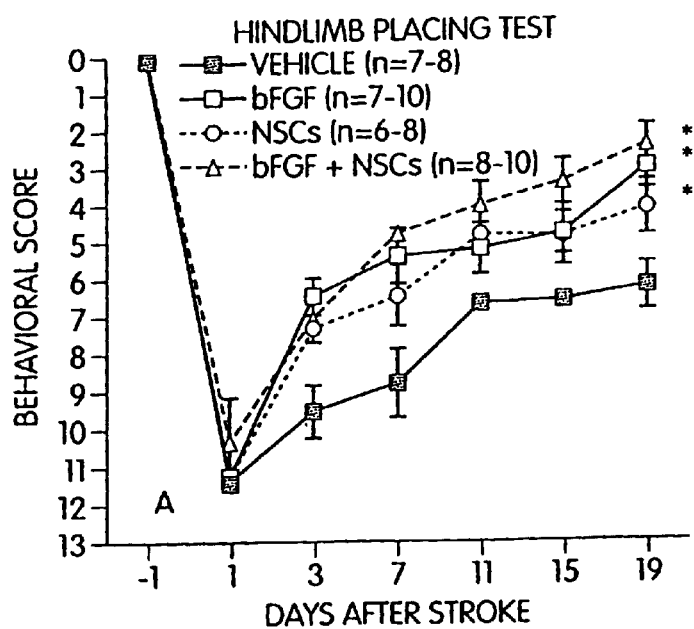

FIG. 2B is a graph that illustrates the results of hindlimb placing tests in a rat stroke model.

Figure 2C:
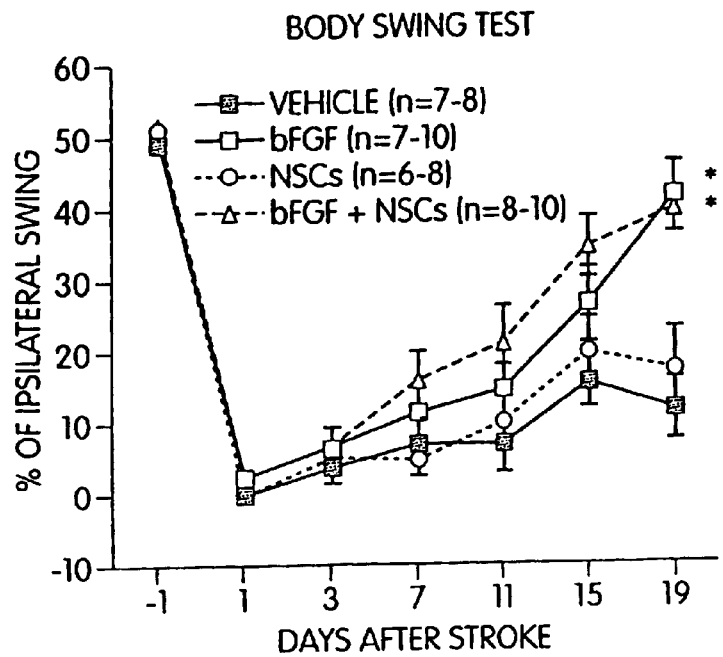

FIG. 2C is a graph that illustrates the results of bodyswing tests in a rat stroke model.

Figure 2D:
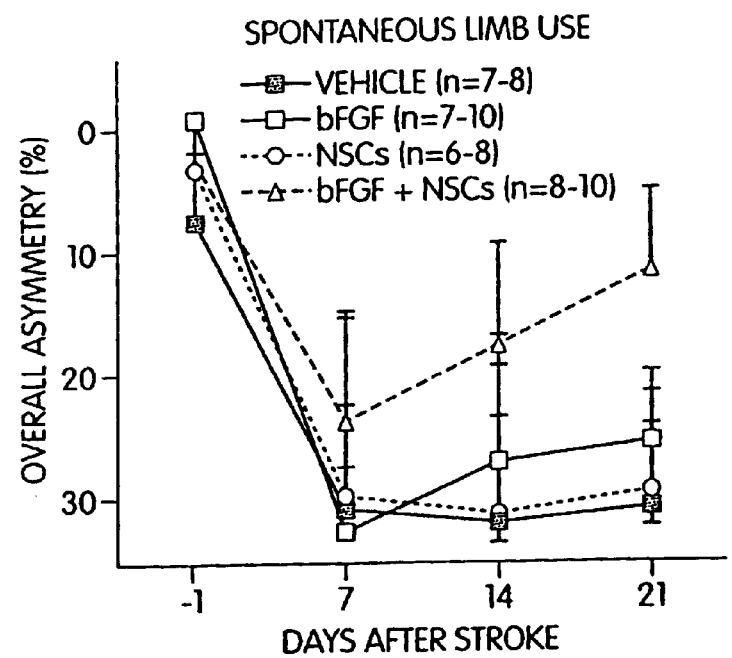

FIG. 2D is a graph showing the results of spontaneous limb use tests in a rat stroke model.

Figure 3:
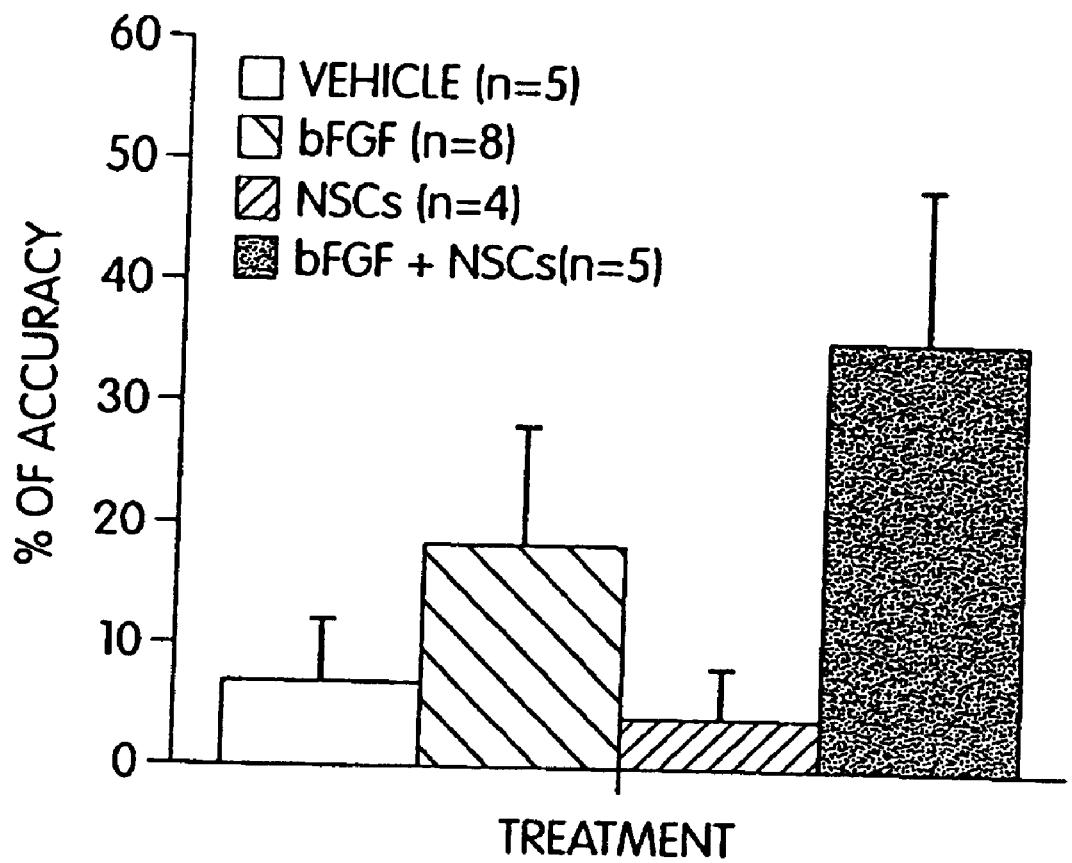

FIG. 3 is a graph depicting the results of paw reaching tests in a rat stroke model.

FIG. 4 presents amino acid sequences for variants of bFGF (SEQ. ID. Nos.1–3).

4. DETAILED DESCRIPTION OF THE INVENTION

4.1 Definitions

The term "brain cells" as used herein refers to cells comprising the brain, including neurons, astroglia, oligodendroglia, and microglia. Many specific cell types belong to each category. For example, neurons include dopaminergic, cholinergic and glutaminergic neurons, to name only a few.

"Bioactive compounds" is intended to include compounds with a desirable effect when used within the context of the invention. Bioactive compounds include many neural stimulants (see below) as well as many compounds that are not considered neural stimulants but that also have desirable effects. For example, immunosuppressants such as the immunophilins (eg. FK506), can exhibit the dual action of preventing rejection of the transplanted cells and providing a neuroprotective activity (Bavetta et al. (1999) *Exp. Neurol.* 158: 382–393). Antibiotics, and particularly tetracyclines, can suppress possible infections and also have beneficial effects on neural cells (Yrjanheikki et al. (1998) *PNAS* 95: 15769–74).

"Cell culture" refers generically to any composition of cells whether actively growing, differentiating, or static. Cell cultures can take on a variety of formats. For instance, a "suspension culture" refers to a culture in which cells are suspended in a suitable medium. A "continuous flow culture" refers to the cultivation of cells in a continuous flow of fresh medium to maintain cell growth or viability. "Continuous expansion" is a method of growing cells by continuous flow culture.

The "central nervous system" (CNS) as used herein, refers to any component of the central nervous system including the brain and spinal cord, the cells and extracellular materials and fluids.

"Conjoint administration" is used herein in reference to the administration of cells and a neural stimulant or bioactive compound to subjects. The term "conjoint administration" is not meant to indicate that the cells and the neural stimulant must be administered at the same time. The components of the conjoint administration may be delivered at different times, at different time intervals and by different means. The administrations should, however, overlap in therapeutic effects.

The term "culture medium" is recognized in the art, and refers generally to any substance or preparation used for the cultivation of living cells.

The term "developmental regulator" is used herein to refer to molecules that modulate development in brain cells or stem cells with the capacity to become brain cells.

By "focal cerebral ischemia" as used herein in reference to the central nervous system, is meant the condition that results from the blockage of a single artery that supplies blood to the brain or spinal cord, resulting in the death of cellular elements in the territory supplied by that artery.

"Global cerebral ischemia" is the diminution of blood flow to the entire brain, often caused by cardiac arrest or hypotension, for example. In global cerebral ischemia, cells that are particularly vulnerable to ischemia tend to die or become injured, resulting in patches of damage distributed around the brain. This differs from the type of damage that occurs in focal cerebral ischemia.

"Guidance molecules" are a class of proteins, normally found in the extracellular matrix, that function to guide cells or cellular processes (axons) to locations required for proper functioning. Examples are the semaphorins, the netrins, the neuropilins, and the ephrins. Perris et al. (2000) *Mech. Dev.* 95: 3–21; Wilkinson (2000) *Int. Rev. Cytol.* 196: 177–244; Van Vactor et al. (1999) *Curr. Biol.* 9: R201–4).

"Hematopoietic stem cells" (HSCs) as used herein are stem cells that can give rise to cells of at least one of the major hematopoietic lineages in addition to producing daughter cells of equivalent potential. Three major lineages of blood cells include the lymphoid lineage, eg. B-cells and T-cells, the myeloid lineage, eg. monocytes, granulocytes and megakaryocytes, and the erythroid lineage, eg. red blood cells. Certain HSCs are capable of giving rise to many other cell types including brain cells. "Multipotent" or "pluripotent" HSCs are HSCs that can give rise to at least three of the major hematopoietic lineages.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with the polypeptide sequence of a bioactive polypeptide of the present invention.

The term "ischemic episode" is used to mean any circumstance that results in a deficient supply of blood to a tissue. Cerebral ischemic episodes result from a deficiency in the blood supply to the brain. The spinal cord, which is also a part of the central nervous system, is equally susceptible to ischemia resulting from diminished blood flow. An ischemic episode may be caused by a constriction or obstruction of a blood vessel, as occurs in the case of a thrombus or embolus. Alternatively, the ischemic episode can result from any form of compromised cardiac function, including cardiac arrest.

The term "neural stimulant" refers to a treatment that affects neural function or activity. Such treatments are typically polypeptide growth factors, for example neurotrophins or fibroblast growth factors. Such treatments also include guidance molecules and non-polypeptide molecules that are active in the brain, such as neurotransmitters, neurotransmitter antagonists or agonists, and developmental regulators. "Neural stimulants" may also be agents that affect the same signaling transduction pathways as those affected by the above listed agents. For example, a chemical that activates bFGF receptor signaling could be used as a neural stimulant. A "neural stimulant" can also include other chemical or electromagnetic treatments that alter the production of molecules that affect neural function or activity (eg. transcranial magnetic stimulation).

"Neural stem cell" (NSC) is used to describe a cell derived from tissue of the central nervous system, or the developing nervous system, that can give rise to at least one of the following fundamental neural lineages: neurons, oligodendroglia and astroglia. Additionally, a neural stem cell must also be able to give rise to new NSCs with similar potential. "Multipotent" or "pluripotent" NSCs are NSCs that are capable of giving rise to all of the above neural lineages as well as cells of equivalent developmental potential.

"Neuronal function" is used to refer generally to all the functions of the nervous system, eg. sensorimotor function and cognitive function.

"Neuroepithelial stem cells" are stem cell populations isolated from fetal neuroepithelial tissue. Such cells may be considered a subset of neural stem cells, as used herein. "Neuroepithelial cells" tend to be multipotent.

"Neurotransmitters" are small molecules released from an axon for action within a synapse. Exemplary neurotransmitters include catecholamines (eg. epinephrine, norepinephrin and dopamine), serotonin, acetylcholine, glutamate and GABA.

A "patient" or "subject" to be treated by the subject method is a mammal, including a human.

As used herein, both "protein" and "polypeptide" mean any chain of amino acid residues, regardless of length or post-translational modification (e.g., glycosylation or phosphorylation). A "bioactive polypeptide", as used herein is a polypeptide that has activity as a neural stimulant. Examples are polypeptide growth factors and guidance molecules. "Bioactive polypeptides" also include active fragments and analogues of the bioactive polypeptides, which possess one or more the biological functions of those factors.

"Polypeptide growth factors" are generally secreted polypeptides, or active fragments thereof, that stimulate cell growth or growth of cell processes (eg. axons, dendrites etc.) in at least on cell type.

"Active fragment" as used in reference to bioactive polypeptides, indicates any portion of a polypeptide that has at least one activity of the full-length polypeptide. Many polypeptides have several different activities and it may be desirable to use an active fragment that has only one or a subset of these activities. The active fragment will produce at least 20%, preferably at least 50%, more preferably at least 70%, and most preferably at least 90% (including up to 100%) of the activity of the full-length polypeptide. An example is bFGF, which can be polymorphic, with observed molecular weights of 17.8, 22.5, 23.1, and 24.2 kDa; all of these forms are biologically active and can be used in the invention.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression construct which is in turn used to transform a host cell to produce the heterologous protein. That is, the polypeptide is expressed from a heterologous nucleic acid.

A "stroke" is a sudden loss of function caused by an abnormality in the blood supply to the brain. Stroke presents with different levels of severity ranging from "transient ischemic attack" or "TIA" (no permanent disability), to "partial nonprogressing stroke" (persistent but no calamitous damage), to "complete stroke" (permanent, calamitous neurological deficit). Ischemia (diminished or stopped blood flow) and infarction (cell damage and death within the zone of ischemia) are the pathologic processes in stroke that lead to neurologic deficits. "Ischemic stroke" is caused by an obstruction of blood vessels supplying the brain. The primary subcategories of ischemic stroke are thrombotic stroke, embolic stroke and lacunar infarctions. "Hemorrhagic stroke" is caused by the rupture of blood vessels supplying the brain. The primary subcategories of hemorrhagic stroke are subarachnoid hemorrhage (SAH) and intracerebral hemorrhage (ICH).

A "therapeutically effective amount" of, eg. cells or neural stimulant, with respect to the subject method, refers to an amount of the therapeutic (in a preparation) which when applied as part of a desired dosage regimen causes an improvement in neuronal function according to clinically acceptable standards.

"Transcranial magnetic stimulation" (TMS) is a method for the stimulation of neurons by briefly generating magnetic fields with typical field strengths between 2 and 4T using coils close to the head (currents in TMS coils can be has high as 8000A). TMS often involves pulses of stimulation with varying pulse and delay times. TMS is known to upregulate monoamines in the brain.

4.2 Overview

The present invention is based in part on the surprising finding that the conjoint administration of cells and neural stimulants promotes greater recovery from CNS damage than either treatment alone. In certain aspects, the invention provides improved methods, compositions and kits for stimulating recovery of damaged brain tissue, whether damage is localized or global. In preferred embodiments, the invention pertains to recovery from ischemia, hypoxia and trauma In certain aspects, the methods of the invention comprise the conjoint administration of stem cells and a neural stimulant, eg. a polypeptide growth factor or other molecule. The conjoint treatment gives a greater degree of recovery than has been possible with either treatment alone. The promise of this approach was recently illustrated in a study wherein the polypeptide growth factor BDNF was administered conjointly with bone marrow cells to improve recovery in a rat stroke model (Chen et al., 2000, *Neuropharmacology* 39: 711–716). The debilitating effects of CNS damage are such that even incremental improvements in recovery can lead to major improvements in a patient's quality of life.

The subject method has wide applicability to the treatment of CNS damage. In this regard, the subject method is useful for, but not limited to, treatment of injury to the brain and spinal cord due to ischemias, hypoxia, traumas, neurodegenerative diseases, infectious diseases, cancers, autoimmune diseases and metabolic disorders. Examples of disorders include stroke, head trauma, spinal trauma, hypotension, arrested breathing, cardiac arrest, Reye's syndrome, cerebral thrombosis, embolism, cerebral hemorrhage, brain tumors, encephalomyelitis, hydroencephalitis, operative and postoperative brain injury, Alzheimer's disease, Huntington's disease, Creutzfeld-Jakob disease, Parkinson's disease, multiple sclerosis and amyotrophic lateral sclerosis.

Thrombus, embolus, and systemic hypotension are the most common causes of cerebral ischemic episodes. Other causes of cerebral ischemia include hypertension, hypertensive cerebral vascular disease, rupture of an aneurysm, an angioma, blood dyscrasias, cardiac failure, cardiac arrest, cardiogenic shock, septic shock, head trauma, spinal cord trauma, seizure, bleeding from a tumor, or other blood loss. With respect to trauma, trauma can involve a tissue insult such as an abrasion, incision, contusion, puncture, compression, etc., such as can arise from traumatic contact of a foreign object with any locus of or appurtenant to the head, neck, or vertebral column. Other forms of traumatic injury can arise from constriction or compression of the CNS tissue by an inappropriate accumulation of fluid (for example, a blockade or dysfunction of normal cerebrospinal fluid or vitreous humor fluid production, turnover, or volume regulation, or a subdural or intracranial hematoma or edema). Similarly, traumatic constriction or compression can arise from the presence of a mass of abnormal tissue, such as a metastatic or primary tumor.

In some cases the damage caused by the above disorders is primarily located in a single region of the brain, eg. focal ischemia, certain traumas and Parkinson's disease. In other cases, damage can be more widespread or distributed across disparate regions of the brain, eg. hypoxia and global ischemia, and Creutzfeld-Jakob disease. Because certain cells of the invention are known to migrate freely throughout the brain, and because growth factors can be provided so as to be generally available to all brain tissues, it is anticipated that the methods and compositions of the invention will be useful in promoting recovery from both global and focal brain damage.

In a general outline, a treatment protocol of the invention involves administering a neural stimulant and stem cells to a patient that has suffered CNS damage. In preferred embodiments, CNS damage was caused by ischemia, hypoxia or trauma. Treatment may include obtaining cells from the patient, optionally enriching for therapeutically useful cells, and administering the cells to the patient. In this way, the patient is not subjected to any foreign cells, which offers the advantage of avoiding immune responses to the cells.

The treatment regimen according to the invention is carried out, in terms of administration mode, timing of the administration, and dosage, so that the functional recovery of the patient from the adverse consequences of the central nervous system injury is improved; for example, the patient's motor skills (e.g., posture, balance, grasp, or gait), cognitive skills, speech, and/or sensory perceptions (including visual ability, taste, olfaction, and proprioception) may improve as result of treatment according to the invention.

While not wishing to be limited to a particular mechanism of action, it is believed that the methods of the invention promote recovery from CNS damage by stimulation of neuronal sprouting and new synapse formation. In cases of stroke, essentially all current treatments focus on infarct reduction and prevention of damage. Therefore, the present invention relates to unconventional and novel methods of treating CNS damage.

4.3 Neural Stimulants and Other Bioactive Factors

Neural stimulants of the invention include treatments, chemical or otherwise, that affect neural function or activity. Such treatments are typically bioactive polypeptides, but non-polypeptide molecules and physical treatments such as transcranial magnetic stimulation are also contemplated.

In one set of preferred embodiments, the neural stimulant is a polypeptide growth factor. The polypeptide growth factor can be administered in a pharmaceutically acceptable carrier, and may also be administered mixed or unmixed with cells. The polypeptide growth factor can be a member of the fibroblast growth factor (FGF) family; the neurotrophin family; the insulin-like growth factor (IGF) family; the ciliary neurotrophic growth factor (CNTF) family; the EGF family; the TGF-beta family; the PDGF family; the VEGF family; the leukemia inhibitory factor (LIF) family; an interleukin (eg. IL-11, IL-6, IL-1); or an oncostatin (eg. oncostatin M). Characteristics and exemplary members of each of these families are given below and in Table 2. In preferred embodiments the polypeptide factor is a human polypeptide factor.

The FGF family contains at least 15 distinct factors that are highly conserved across mammalian species, although individual family members can be highly divergent from each other (generally 30–70% sequence identity). FGFs are secreted proteins that share a basic tertiary structure composed of 12 beta-strands in a beta-trefoil fold. Most family members have mitogenic effects on various cell types and also bind heparin. Exemplary members of the FGF family include: basic FGF (bFGF, FGF-2), acid FGF (aFGF, FGF-1), FGF-3 (int-2), FGF4 (hst/kFGF), FGF-5, FGF-6, FGF-7 (KGF), FGF-8 (AIGF), and FGF-9 (GAF). (Stauber et al. (2000) *PNAS* 97: 49–54; Wong et al. (1998) *J. Biol. Chem.* 273: 18617–18622; Szebenyi et al. (1999) *Int. Rev. Cytol.* 185: 45–106).

The neurotrophin family includes several related, secreted factors that exert their effects primarily on the nervous system. Neurotrophins are generally produced as precursor proteins that are highly processed to give the mature forms. Mature neurotrophins carry a set of six cysteines that engage in disulfide bonding in the order 1–4 (ie. the first and fourth cysteines form a disulfide bond), 2–5 and 3–6. Typically, neurotrophin family members have a surface composed of 3 antiparallel beta-strands, and dimerization occurs along this surface. Exemplary members of the neurotrophin family are: nerve growth factor (NGF), brain-derived neurotrophic factor (BDNF), neurotrophin 3 (NT3), neurotrophin 4/5 (NT4/5) and neurotrophin 6. (Lewin et al. (1996) *Annu. Rev. Neuroscience* 19:289–317).

The insulin-like growth factor family includes secreted proteins with a sequence and structure similar to that of insulin and a molecular weight typically in the range of 5–10 kDa. These factors can be found in the bloodstream, usually associated with one of six IGF binding proteins. Exemplary members of the family include IGF-1 and IGF-2. IGF-1 and -2 are known to promote recovery from various insults to the CNS. (Daughaday et al. (1989) *Endocr. Rev.* 10: 68–91; Rajaram et al. (1997) *Endocr. Rev.* 18: 801–831; Jones et al. (1995) *Endocr. Rev.* 16: 3–34).

The epidermal growth factor family is a large family of related secreted factors. Members of the EGF family share at least 30% sequence homology and a set of six conserved cysteine residues in the C-terminal end of the protein. Most such proteins also contain an EGF-like domain, which is a particularly well-characterized domain that is also present in many non-EGF family member proteins. EGF family members are normally processed from larger precursors. Exemplary members of the EGF family include EGF, TGF-alpha, HB-EGF (heparin-binding EGF), amphiregulin, betacellulin, vaccinia growth factor and neu differentiation factor. (Aviezer et al. (1 994) 91: 12173–12177; Higashyama et al. (1992) *J. Biol. Chem.* 267: 6205–6212; Pelles et al. (1992) *Cell* 69:205–216).

The TGF-beta superfamily is an important class of molecules involved in cell-cell signaling and development in a wide range of organisms and cell types. Members of the family are initially synthesized as larger precursor molecules with an amino-terminal signal sequence and a pro-domain of varying size (Kingsley, D. M. (1994) *Genes Dev.* 8:133–146). The precursor is then cleaved to release a mature carboxy-terminal segment of 110–140 amino acids. The active signaling moiety is comprised of hetero- or homodimers of the carboxy-terminal segment (Massague, J. (1990) *Annu. Rev. Cell Biol.* 6:597–641). The active form of the molecule then interacts with its receptor, which for this family of molecules is composed of two distantly related transmembrane serine/threonine kinases called type I and type II receptors (Massague, J. et al. (1992) *Cell* 69:1067–1070; Miyazono, K. A. et al. *EMBO J.* 10:1091–1101). TGF-beta binds directly to the type II receptor, which then recruits the type I receptor and modifies it by phosphorylation. The type I receptor then transduces the signal to downstream components (Wrana et al, (1994) *Nature* 370:341–347). In general, members of the TGF-beta superfamily have a set of nine highly conserved cysteine residues that are involved in disulfide bonding both within and between monomers of the mature, dimerized signaling protein (Griffith et al. (1996) *PNAS* 93: 878–883; Luo et al. (1995) *PNAS* 92: 11761–11765; Schlunegger et al. (1993) *J. Mol. Biol.* 231: 445–58; Daopin et al. (1993) *Proteins* 17: 176–92; Murray-Rust et al. (1993) *Structure* 15: 153–9; Archer et al. (1993) *Biochemistry* 32: 1164–71; Daopin et al. (1992) *Science* 257: 369–373; Schlunegger et al. (1992) *Nature* 358: 430–434; Hinck et al. (1996) *Biochemistry* 35: 8517–34; Mittl et al. (1996) *Protein Sci.* 5:1261–71).

The transforming growth factor beta family is a very large family of proteins including the TGF-beta subfamily, the bone morphogenesis protein (BMP) subfamily, the activin subfamily, and others. Exemplary members of the TGF-beta subfamily include TGF-beta-1, -2, -3, -4 and -5. Exemplary members of the BMP subfamily include osteogenic protein 1 (OP-1, BMP-7) and BMP-9. (Ren et al. (2000) *Neuropharmacology* 39: 860–865; Lopez-Coviella et al. (2000) *Science* 289: 313–316; Withers et al. (2000) *Eur. J. Neurosci.* 12: 106–116).

The vascular endothelial growth factor (VEGF) family is a group of secreted proteins that act as potent mitogens in embryonic and somatic angiogenesis. VEGF proteins, including VEGF itself, bind to cell surface receptors of the kinase domain receptor family (KDR) and fms-like tyrosine kinase group (Flt receptors). VEGF proteins form a homodimer with a cystine knot structure. Platelet-derived growth factor (PDGF) shares only limited sequence similarity with VEGF (19%) but has substantial structural similarity. PDGF and related family members are also cystine knot proteins and bind to their receptors in a similar manner. (Lobsiger et al. (2000) *Glia* 30: 290–300; Sun et al. (1995) *Annu. Rev. Biophys. Biomolec. Struct.* 24: 269–291; Muller et al. (1997) *Structure* 5: 1325–1338; Jiang et al. (2000) *EMBO J.* 19: 3192–3203; Muller et al. (1997) *PNAS* 94: 7192–7197).

Interleukins are secreted polypeptide factors that mediate signaling between immune cells. Many interleukins are known to have effects on the brain, particularly IL-1α and β, IL-6 and IL-11. (Van Wagoner et al. (1999) *J. Neuroimmunol.* 100: 124–139; Ling et al. (1998) *Exp. Neurol.* 149: 411–23; Mehler et al. (1993) *Nature* 362: 62–5). Intriguingly, IL-6 and IL-11 both act in part through a receptor protein gp130 that acts as a receptor for ciliary neurotrophic factor (CNTF), leukemia inhibitory factor (LIF) and oncostatin M. Thus all these factors may have similar roles in modulating neuronal function and development. (Benigni et al. (1995) *Mol. Med.* 1: 568–75; Benigni et al. (1996) *Blood* 87: 1851–4; Murphy et al. (1997) *Prog. Neurobiol.* 52: 355–78).

TABLE 1

Polypeptide Growth Factors

| Family | Exemplary subfamilies | Exemplary Members |
|---|---|---|
| FGF | | bFGF, aFGF, FGF-3, FGF-4, FGF-5, FGF-6, FGF-7, FGF-8, FGF-9 |
| Neurotrophins | | NGF, BDNF, NT3, NT4/5, NT-6 |
| IGF | | IGF-1, IGF-2 |
| EGF | | EGF, TGF-alpha, HB-EGF, amphiregulin, betacellulin, vaccina growth factor and neu |
| TGF-beta | TGF-beta | TGF-beta-1, -2, -3, -4 and -5 |
| | BMP | OP-1, BMP-9 |
| | Activin | InhibinβA, InhibinβB and InhibinβC |
| VEGF | | VEGF |
| PDGF | | PDGF |
| | | LIF |
| CNTF | | CNTF |
| Interleukins | | IL-1α, IL-1β, IL-6, IL-11 |
| Oncostatins | | Oncostatin M |

Furthermore, the nomenclature in the field of polypeptide factors is complex, primarily because many factors have been isolated independently by different groups of researchers and, historically, named for the type of tissue that was used as an assay in the process of purifying the factor. Basic FGF has been referred to in scientific publications by a number of different names, and has multiple family members. These include leukemic growth factor, macrophage growth factor, embryonic kidney-derived angiogenesis factor 2, prostatic growth factor, astroglial growth factor 2, endothelial growth factor, chondrosarcoma growth factor, cartilage-derived growth factor 1, eye-derived growth factor 1, heparin-binding growth factors class 11, myogenic growth factor, human placenta purified factor, uterine-derived growth factor, embryonic carcinoma-derived growth factor, human pituitary growth factor, adipocyte growth factor, prostatic osteoblastic factor, and mammary tumor-derived growth factor. Thus, any factor referred to by one of the aforementioned names is considered within the scope of the invention. Furthermore, effort has been made to use commonly accepted names for factors, and any factor listed here is considered within the scope of the invention regardless of whether it is known to others by a different name.

The invention can also employ bioactive analogues of the aforementioned growth factors, which possess one or more of the biological functions of those factors. An example is bFGF, which can be polymorphic, with observed molecular weights of 17.8, 22.5, 23.1, and 24.2 kDa; all of these forms are biologically active and can be used in the invention. It is possible to identify bioactive analogues of the aforementioned factors. Such analogues, when designed to retain at least one activity of a naturally occurring form of the polypeptide, are considered functional equivalents. Bioactive analogues may also include molecules that are not polypeptides but nonetheless mimic activities of a polypeptide growth factor. Bioactive analogues may also have advantageous properties, such as enhanced efficacy or more desirable stability properties (e.g., ex vivo shelf life and resistance to proteolytic degradation in vivo). For example, the analogue may be rendered either more stable or less stable to proteolytic degradation or other processes which result in destruction of, or otherwise inactivation of, the factor. A short half-life can give rise to more transient biological effects can therefore allow tighter control of protein levels within or around a particular tissue. A longer half-life can increase the potency of the factor.

In certain embodiments, bioactive polypeptides of the invention comprise a polypeptide with an amino acid sequence that is at least 30% identical to the bFGF sequence set forth in one of SEQ. ID. Nos. 1–3. In preferred variations, such bioactive polypeptides comprise a polypeptide with an amino acid sequence that is at least 40%, 50%, 60%, 70%, 80%, 90%, 95%, 98%, 99% or 100% identical to one of SEQ. ID. Nos.1–3.

Methods for generating such bioactive analogues are well known in the art. In general, variations of a polypeptide factor can be generated by introducing changes into a nucleic acid sequence encoding the factor. The altered nucleic acid can then be expressed to produce altered polypeptides, and the polypeptides can be assayed for various properties. Changes in nucleic acid sequences can be made individually to introduce particular, desired changes. Alternatively, libraries of semi-randomly generated variants may be produced and screened for activity.

There are many ways by which a library of potential bioactive analogs can be generated. In an illustrative embodiment, the amino acid sequences for a population of bFGF homologs or other related proteins are aligned, preferably to promote the highest homology possible. Such a population of variants can include, for example, bFGF homologs from one or more species, e.g. murine and chicken, or bFGF homologs from the same species but which differ due to mutation. Amino acids which appear at each position of the aligned sequences are selected to create a degenerate set of combinatorial sequences. In a preferred embodiment, the variegated library of bFGF variants is generated by combinatorial mutagenesis at the nucleic acid level, and is encoded by a variegated gene library. For instance, a mixture of synthetic oligonucleotides can be enzymatically ligated into gene sequences such that the degenerate set of potential bFGF sequences are expressible as individual polypeptides, or alternatively, as a set of larger fusion proteins (e.g. for phage display) containing the set of bFGF sequences therein.

Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired bioactive analogs. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Alternatives to the above combinatorial mutagenesis also exist. For example, bFGF analogs can be generated, for example, alanine scanning mutagenesis and the like (Ruf et al. (1994) *Biochemistry* 33:1565–1572; Wang et al. (1994) *J. Biol. Chem.* 269:3095–3099; Balint et al. (1993) *Gene* 137:109–118; Grodberg et al. (1993) *Eur. J. Biochem.* 218:597–601; Nagashima et al. (1993) *J. Biol. Chem.* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol. Cell Biol.* 12:2644–2652; McKnight et al. (1982) *Science* 232:316); by saturation mutagenesis (Meyers et al. (1986) *Science* 232:613); by PCR mutagenesis (Leung et al. (1989) *Method Cell Mol Biol* 1:11–19); or by random mutagenesis (Miller et al. (1992) *A Short Course in Bacterial Genetics*, CSHL Press, Cold Spring Harbor, N.Y.; and Greener et al. (1994) *Strategies in Mol Biol* 7:32–34).

The above methods may be generalized to other polypeptide factors in addition to bFGF.

Having generated one or more variants of a bioactive factor, various methods may be used to identify variants with the desired properties. Whether one or more changes in the amino acid sequence of a peptide results in a bioactive analog can be readily determined by assessing the ability of the variant peptide to produce a response in cells in a fashion similar to the wild-type peptide or competitively inhibit such a response. In addition, the ability of such a polypeptide to bind to its receptor can also be determined. For example, bFGF normally binds to the receptors FGFR1 and FGFR2. This binding is also stimulated by heparin binding. These properties could be checked to verify that a bFGF variant is active.

A wide range of techniques are known in the art for screening gene products of combinatorial libraries, and for screening cDNA libraries for gene products having a certain property. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of variant sequences created by combinatorial mutagenesis techniques.

In one possible screening assay, the gene library is expressed as a fusion protein on the surface of a viral particle. For instance, in the filamentous phage system, foreign peptide sequences can be expressed on the surface of infectious phage. These phage can be applied to affinity matrices at very high concentrations, allowing screening of a large number of phage simultaneously. If a particular phage is recovered from an affinity matrix in low yield, the phage can be amplified by another round of infection in a suitable host, such as *E. coli*. The group of almost identical *E. coli* filamentous phages M13, fd., and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624628; and Barbas et al. (1992) *PNAS* 89:4457–4461).

In another embodiment, the combinatorial library is designed to be extracellularly presented (e.g. as it occurs naturally) or optionally, secreted (e.g. the polypeptides of the library all include a signal sequence). The library can be transfected into a eukaryotic cell that can be co-cultured with cells which express a functional receptor for the desired bioactive fragment. For example, one might use cells expressing a bFGF receptor to identify bioactive variants of bFGF. Bioactive analogs secreted by the cells expressing the combinatorial library will diffuse to neighboring receptor positive cells and induce a phenotypic change. Phenotypic changes may be detected using, for example, antibodies directed to epitopes that are either created or destroyed in response to factor treatment.

Each of these analogs can subsequently be screened for further biological activities. For example, receptor-binding analogs isolated from the combinatorial library can be tested for their effect on cellular proliferation relative to the wild-type form of the protein. Alternatively, one could screen the analogs for stability in vitro or in vivo. The activity of such analogs can also be assessed in animal models. For example, the ability of an analog to improve neural function in a rat stroke model could be assessed to verify that an analog has the appropriate bioactivity.

Many different types of mutations can give rise to bioactive analogs. For example, conservative changes in the amino acid sequence can be expected to give rise to analogues that retain one or more bioactivity. It is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4)

uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, W H Freeman and Co.: 1981).

In other embodiments, chemically modified bioactive factors are contemplated. A polypeptide may be chemically modified to create derivatives by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or at the C-terminus of the polypeptide. For instance, a bioactive factor can be generated which includes a moiety, other than sequences naturally associated with the protein, that binds a component of the extracellular matrix and enhances localization of the analog to cell surfaces. For example, sequences derived from the fibronectin "type-III repeat", such as a tetrapeptide sequence R-G-D-S (Pierschbacher et al. (1984) *Nature* 309:30–3; and Komblihtt et al. (1985) *EMBO* 4:1755–9) can be added to a polypeptide factor to support attachment of the chimeric molecule to a cell through binding ECM components (Ruoslahti et al. (1987) *Science* 238:491497; Pierschbacheret al. (1987) *J. Biol. Chem.* 262:17294–8.; Hynes (1987) *Cell* 48:549–54; and Hynes (1992) *Cell* 69:11–25).

Alternatively, polypeptide growth factors useful in the invention can consist of active fragments of the factors. The activity of any given fragment can be readily determined in by methods such as those described above. For example, a fragment of bFGF that, when administered according to the methods of the invention described herein, is shown to improve performance in functional tests that is comparable to the performance that is produced by administration of the full-length bFGF polypeptide, would be an "active fragment" of bFGF. Such active fragments are described, e.g., in Baird and Gage (1997) Proc. Natl. Acad. Sci. U.S.A., 94 (13): 7047–52. It is well within the abilities of skilled artisans to determine whether a polypeptide growth factor, regardless of size, retains the functional activity of a full length, wild-type polypeptide growth factor.

The polypeptide factors useful in the invention are preferably substantially purified from their source material, be it cell culture, tissue sample, biological fluid, etc. Substantially purified means that the purified material is at least 60% by weight (dry weight) the polypeptide of interest, e.g., a bFGF polypeptide. Preferably, the polypeptide composition is at least 75%, more preferably at least 90%, and most preferably at least 99%, by weight, the polypeptide of interest. Purity can be measured by any appropriate standard method, e.g., column chromatography, polyacrylamide gel electrophoresis, or HPLC analysis. Substantially purified polypeptides can then be combined with other desired components, such as carriers or cells, to give a composition that is less than 60% composed of polypeptide, so long as the polypeptide is at sufficient concentration to be effective when administered to a patient.

The polypeptide factors useful in the invention can be naturally occurring, synthetic, or recombinant molecules consisting of a hybrid or chimeric polypeptide with one portion, for example, being bFGF, and a second portion being a distinct polypeptide. These factors can be purified from a biological sample, chemically synthesized, or produced recombinantly by standard techniques (see. e.g., Ausubel et al., Current Protocols in Molecular Biology, New York, John Wiley and Sons, 1993; Pouwels et al., Cloning Vectors: A Laboratory Manual, 1985, Suppl. 1987).

Although polypeptide growth factors are currently most preferred for use in combination with the cells according to the invention, other treatment modalities are considered neural stimulants that can be combined with cells according to the invention as well. For example, transcranial magnetic stimulation upregulates monoamines in the brain and is therefore expected to have beneficial effects in conjoint administration with cells.

One group of non-polypeptide neural stimulants that can be used as neural stimulants are neurotransmitter agonists or antagonists. Examples are antidepressants such as Prozac, amphetamines, Ritalin, and tricyclic antidepressants such as Elavil.

Other useful molecules are differentiation factors such as retinoic acid which are capable of priming cells to differentiate into functioning neurons.

Another class of molecules is the so-called guidance molecules, which are a class of proteins, normally found in the extracellular matrix, that function to guide cells or cellular processes (axons) to locations required for proper functioning. Examples are the semaphorins, the netrins, the neuropilins, and the ephrins.

In addition to the above neural stimulants, all of which have well-established effects on the brain, it is anticipated that other bioactive compounds that are not considered neural stimulants might be useful in combination with cells. These alternative compounds are generally compounds with well-known effects on other parts of the body with more recently discovered effects on cells of the CNS.

One group of alternative compounds includes immunosuppressant molecules that are currently used to inhibit rejection of allografts. A preferred class of such molecules are the immunophilins, such cyclosporin, FK506, and thalidomide. These molecules can exhibit dual action of preventing rejection of the transplanted cells and providing neuroprotective function. Another group of alternative stimulants is the tetracyclines, classically known for their antibiotic effects, but also possessing desirable neuroprotective effects.

4.4 Cells

Many different cell types, or mixtures thereof, may be administered to a subject. While not wishing to be limited by theory, it is postulated that administered cells may affect the brain in multiple ways. Cells may themselves become established in the brain and form functional connections with neurons. Additionally or alternatively, cells may produce factors that stimulate the endogenous nerve cells to form new processes and connections. Finally, cells might act to scavenge or otherwise remove or inactivate compounds that inhibit recovery from CNS damage. In view of these possibilities, it is understood that essentially any cell possessing one of the above qualities, and particularly stem cells but potentially even terminally differentiated cells, might have beneficial effects on brain function. Examples of terminally differentiated cell types that are known to have beneficial scavenging capabilities are activated lymphocytes and macrophages.

In certain embodiments, the cells of the invention are preferably stem cells that have the capability of giving rise to brain cells in vivo. Particularly preferred cells are multipotential stem cells. Such cells can be grown in vitro for clinical use. In preferred embodiments, stem cell types that can be used in the invention include neural stem cells, hematopoietic stem cells, embryonic stem cells, teratocarcinoma cell lines, and other stem cell types.

The term "stem cell" as used herein refers to cells with the capacity for unlimited or prolonged self-renewal that can give rise to more than one type of more differentiated descendant. Preferred stem cells can undergo at least 10 cell divisions (under appropriate conditions) and still maintain stem cell characteristics. Particularly preferred stem cells can undergo at least 25, 50 or 100 rounds of division without losing stem cell characteristics. With respect to cells, the terms "give rise to" and "produce" are used to mean not just the immediate daughter cells, but all the cells that can eventually trace ancestry to that cell. "Give rise to" and "produce" also refer to changes in cell type that might occur without a cell division event. Some differentiated cells also have the capacity to give rise to cells of greater developmental potential. Such capacity may be natural under particular circumstances, or may be induced artificially upon treatment with various factors. In either case, the cells may be considered a type of stem cell for the purposes of the invention. Such stem cells may be referred to as "induced stem cells" or "differentiated stem cells". "Processed stem cells" refers to stem cells that have been in any way disturbed from their natural cellular environment. This includes centrifugation, dissociation, dispersion or other processing. The stem cells contained in an unprocessed tissue sample are not considered "processed stem cells".

Stem cells are usually rare cell types mixed with other, more differentiated cells. For the purposes of the invention, it is possible to use cell suspensions that comprise only a minority of stem cells. Such an approach is particularly useful with cells derived from a stem cell rich tissue, eg. bone marrow. In preferred embodiments, stem cells are enriched such that they are at least 50% pure, meaning that at least 50% of the cells are stem cells at the time of administration to a subject. In particularly preferred embodiments, stem cells are at least 60%, 70%, 80% or 90% pure.

4.4.1 General Methods for Stem Cell Culture and Propagation

Various techniques may be employed to isolate the stem cells of the invention. Typically, stem cells will be obtained from a tissue sample (eg. blood, bone marrow, fetal or adult brain tissue, etc.) wherein the desired stem cells constitute a small percentage of the cells present. In preferred embodiments, the tissue sample is dissociated into a cell suspension and optionally, various methods are used to enrich for stem cells. Preferred procedures for dissociation of the tissue sample are ones that result in as little cell death as possible. For example, stem cells can be dissociated from tissue samples by mechanical means, e.g., mechanically sheared off with a pipette. In other instances, it will be possible to dissociate the stem cells from the surrounding tissue by enzymatic digestion. Fluid tissue samples, such as blood, can be fractionated by centrifugation and resuspension of certain fractions, if appropriate. Separation of different cell types and extracellular materials may also be achieved by centrifigation or settling in a density gradient of, for example Ficoll. Stem cell populations may be enriched based on their tendency for continued cell growth as well as specific cellular markers, e.g., using affinity separation techniques or fluorescence activated cell sorting (FACS).

There are a large number of culture media that exist for culturing cells from animals. Some of these are complex and some are simple. While it is expected that stem cells may grow in complex media, it will generally be preferred that the explants be maintained in a simple medium, such as Dulbecco's Minimal Essential Media (DMEM), in order to allow more precise control over the activation of certain cell populations in a tissue sample. The cultures may be maintained in any suitable culture vessel, such as a 12 or 24 well microplate, and may be maintained under typical culture conditions for cells isolated from the same animal, e.g., such as 37° C. in 5% $CO_2$. The cultures may be shaken for improved aeration, the speed of shaking being, for example, 12 rpm.

In general, stem cells can be enriched by detecting and sorting based on identifying characteristics of the desired cells. For example, monoclonal antibodies are particularly useful for identifying markers (surface membrane proteins, e.g., receptors) associated with particular cell lineages and/or stages of differentiation. Procedures for separation of the subject progenitor cell may include magnetic separation, using antibody coated magnetic beads, affinity chromatography, and "panning" with antibody attached to a solid matrix, e.g., plate, or other convenient technique. Techniques providing accurate separation include fluorescence activated cell sorting, which can have varying degrees of sophistication, e.g., a plurality of color channels, low angle and obtuse light scattering detecting channels, impedance channels, etc.

Antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the cells.

In addition to using antibodies, it is possible to use other proteins that bind to the surface of desired cells. For example, if a desired cell specifically expresses the EGF receptor, then labeled EGF could be used to detect those cells in much the same way as described for the antibodies above. Certain dyes also stain particular cell populations and can be used as part of a method for obtaining the desired cells. Stem cells also typically have a distinctive morphology. Stem cells usually have a large nucleus with a relatively small amount of cytoplasm.

The selection methods described above may be combined with the use of selective growth conditions to provide further enrichment. For example, natural and recombinantly engineered cells can be provided as feeder layers to the instant cultures. Such cells can also produce an extracellular matrix that can be used as a substrate for selection methods.

It is also possible to contact cell mixtures with an agent that causes proliferation of one or more populations of cells. For instance, a mitogen, e.g., a substance that induces mitosis and cell transformation of a particular stem cell type can be used to cause the amplification of that population. In this way, cells that are not responsive to the particular factor tend not to divide while those that are responsive divide and become a greater proportion of the cell population.

After enrichment it is important to verify that cells obtained have the appropriate characteristics. Cells of the present invention can be characterized based on responsiveness to growth factors, specific gene expression, antigenic markers on the surface of such cells, dye staining and/or basic morphology. It is also valuable to determine the types of cells that a particular stem cell population can give rise to. Stem cells can be induced to differentiate into various cell types by changing the environmental conditions. For example, the subject progenitor cells can be recombined with the corresponding embryonic tissue to see if the embryonic tissue can instruct the adult cells to codevelop and codifferentiate. Stem cells can be implanted into one of a number of regeneration models used in the art, e.g., neural stem cells will colonize and differentiate in the brain of a rat that has been lesioned (Gage et al. (1995) *Proc. Natl. Acad. Sci. USA*, 92: 11879–11883; Flax et al. (1998) *Nature Biotechnology* 16:1033–1039). Stem cells may be genetically labeled by transfection with a piece of foreign DNA. This labeling allows identification of stem cell descendants from among the host cells. Alternatively, the progenitor cells can be contacted with one or more growth or differentiation factors which can induce differentiation of the cells. Differentiated cell types can be identified using the same general methods used to identify stem cells, eg. cell surface marker, dye staining etc.

In certain situations it is desirable to measure cell proliferation. Such methods most commonly include determining DNA synthesis characteristic of cell replication. There are numerous methods in the art for measuring DNA synthesis, any of which may be used according to the invention. In an embodiment of the invention, DNA synthesis has been determined using a radioactive label ($^3$H-thymidine) or labeled nucleotide analogues (BrdU) for detection by immunofluorescence.

Growth factors may also be provided in the medium to selectively expand certain cell populations or to encourage the production of differentiated cell types.

Cells can be sorted by positive and negative selection. For example, positive or negative selection may be achieved by using one or more biotinylated antibodies, specific for factors on the surface of the target cells. The biotinylated antibodies are introduced into the cell culture. After a specified incubation time any biotinylated antibodies which have not formed a complex with the target cells are rinsed away. Immobilized avidin matrix is then added to the cell suspension. The immobilized avidin matrix binds to the biotinylated antibody/antigen complex. This suspension can then be centrifuged to separate the avidin matrix. Alternatively, the avidin may be coupled to magnetic beads such that the cells bound to the antibody are magnetically separated from unbound cells. If the selection is positive, cells bound to the antibody are resuspended in nutrient medium for continued growth. If the selection is negative, bound cells may be disposed of, while the remaining unbound cells are resuspended for further growth.

Clearly, many other techniques may be utilized for both positive and negative selection, as long as the desired affinity is provided by the selection element.

Hematopoietic Stem Cells

Mammalian blood cells provide for an extraordinarily diverse range of cell types. Three major lineages of blood cells include the lymphoid lineage, eg. B-cells and T-cells, the myeloid lineage, eg. monocytes, granulocytes and megakaryocytes, and the erythroid lineage, eg. red blood cells. Hematopoietic stem cells (HSCs) are cells that can give rise to cells of at least two of the above lineages in addition to producing daughter cells of equivalent multipotency. In preferred embodiments, the HSCs can give rise to three major blood cell lineages. In addition to giving rise to blood cells, HSCs are capable of differentiating into many other cell types, including brain cells (Eglitis and Mezey (1997) *Proc. Natl. Acad. Sci. USA*, 94: 4080–4085).

HSCs can be isolated from a variety of tissue types. Bone marrow cells are a good source of HSCs. Bone marrow cells may be obtained from a source of bone marrow, e.g., iliac crests, tibiae, femora, spine, or other bone cavities. Other sources of human hematopoietic stem cells include embryonic yolk sac, fetal liver, fetal and adult spleen and blood, including adult peripheral blood.

HSCs can be identified both by the types of cells they give rise to and by various cytological markers. HSCs often extrude certain dyes, such as Hoechst 33324 and Rhodamine 123 (Bhatia et al. (1998) *Nature Med.* 4:1038). Such dye staining properties can be used to identify HSCs among other cells of the circulatory system. Antibodies that react with certain cell markers can also be used to identify and purify HSCs. For example, mAb AC133 is thought to specifically bind to HSCs (Miraglia et al. (1997) *Blood* 90:5013). The Thy-1 molecule is a highly conserved protein present in the brain and hematopoietic system of rat, mouse and man. The Thy-1 molecule has been identified on rat, mouse and human HSCs and can be useful in identifying HSCs (U.S. Pat. No. 5,914,108). Many HSCs are CD34+ and/or CD38+ as well (U.S. Pat. No. 5,840,580). A population of HSCs will often have some variation in cell surface markers and a positive identification may be made on the basis of the presence of at least two of the above cytological markers.

HSCs can also be distinguished from other more differentiated cell types by the absence of certain markers. CD3, CD7, CD8, CD10, CD14, CD15, CD19, CD20 and CD33 are all typically absent from HSCs. The absence of several of the above markers adds confidence to the identification of HSCs. Morphology may also help distinguish an HSC, as described above.

It is understood that HSCs may be identified by an aggregation of multiple traits, such as morphology, the presence of certain markers, the absence of other markers, and the types of cells that the putative HSCs can give rise to. A positive identification does not typically require detection of all of the above markers.

The culturing of HSCs to give rise to differentiated stem cells can be achieved in many ways. For example, cells may be cultured in a defined, enriched medium such as Iscove's Modified Dulbecco's Medium (IMDM), generally composed of salts, amino acids, vitamins, antibiotics and fetal calf serum. Cultures supplemented with hydrocortisone tend to give rise to myeloid cells, while cultures lacking cortisone tend to give rise to B lymphocytes. To demonstrate that HSCs can develop in cells of the erythroid lineage, various conventional methods can be used. For example culturing on methylcellulose culture can stimulate formation of erythroid cells. (U.S. Pat. Nos. 5,840,580 and 5,914,108; Metcalf (1977) In: Recent Results in Cancer Research 61. Springer-Verlag Berlin, pp. 1–227).

Neural Stem Cells

Neural stem cells are cells derived from tissue of the adult or developing nervous system that can differentiate into at least one of the following fundamental neural lineages: neurons, oligodendroglia and astroglia. Additionally, neural stem cells can also give rise to new NSCs with similar potential. In preferred embodiments, neural stem cells are multipotential and give rise to cells of most or all of the fundamental neural lineages.

Each of the fundamental neural lineages can be distinguished by detecting lineage-specific proteins, as well as by morphology. Neurons can be recognized by detecting, for example, microtubule-associated protein 2 (MAP2), tau, certain beta-tubulins (eg. TuJ1, beta-tubulin type III), certain neurofilament proteins (eg. neurofilament L or M), neuron-specific enolase, or NeuN. Oligodendrocytes can be recognized by detecting galactocerebrosidase (GalC), CNPase, myelin basic protein, or O4 protein. Astrocytes can be recognized by the presence of glial fibrillary acid protein (GFAP). Certain NSCs can themselves be recognized by the presence of vimentin or nestin. Typically detection is done by standard immunostaining techniques using antibodies that recognize the desired proteins (Villa et al. (2000) *Exp. Neurology* 161: 67–84). Antibodies for each of the above markers are available from one or more of the following companies: Chemicon, Sigma-Aldrich, Boehringer-Mannheim, Santa Cruz Biotechnology, Dakopatts AB (Sweden). The expression of genes encoding lineage-specific proteins may also be used to distinguish cells of different lineage. Detection of gene expression can also be measured by a variety of well-known techniques including in-situ hybridization, fluorescent in-situ hybridization, quantitative rtPCR, Northern blot.

Preferred methods for isolating and propagating NSCs are described in the following publications: Snyder et al., U.S. Pat. No. 5,958,767; McKay et al., U.S. Pat. No. 5,270,191; Johe, K., U.S. Pat. No. 5,753,506; Carpenter, M., U.S. Pat. No. 5,968,829, Weiss et al. U.S. Pat. No. 5,750,376. All of these are herein incorporated by reference.

In general, neural stem cells are maintained in a proliferative, undifferentiated state in the presence of one or more growth factors, for example: bFGF, EGF, TGF-alpha, LIF, or aFGF. Preferred factors are bFGF or EGF. Withdrawal of such factors allows differentiation into cells of distinct lineage. The lineages formed depend on the environment. For example, certain NSCs introduced into the brain can form all of the different brain cell types depending on the particular environment each cell finds itself in. In culture, the developmental pathway can be influenced by many factors. For example, CNTF can induce differentiation into astrocytes, PDGF can induce formation of neurons, and thyroid hormone (T3) can induce formation of oligodendroglial cells.

In preferred embodiments, neural stem cells are obtained as described in U.S. Pat. No. 5,958,767. This method is described here in brief as an example of a specific method for preparing NSCs. It is understood that many such methods exist and that the details of this method can be modified to give similar results. In brief, a suspension of primary dissociated neural cells is prepared from the telencephalon of a 15 week gestational fetus. The suspension is plated on uncoated tissue culture dishes with Dulbecco's Modified Eagle Medium (DMEM) plus F12 medium (1:1) supplemented with N2 medium (Gibco) to which bFGF and heparin or EGF is added. Cell aggregates are dissociated when they grow to a size larger than 10 cell diameters in size. Dissociation is performed with trypsin and the NSC cell suspension is resuspended in growth medium. Dissociated stem cells can be plated on poly-L-lysine coated slides in DMEM+fetal bovine serum to encourage differentiation. Astrocyte differentiation can be stimulated by co-culturing with primary dissociated cultures of newborn CD-1 mouse brain. Cells may be transfected so as to express a gene that promotes cell division, allowing cell proliferation in vitro without added growth factors. Processes for generating transfected cells are well known in the art. In preferred embodiments, the cells are transfected with an amphotrophic replication-incompetent retroviral vector, and the mitogenic gene is expressed from the viral LTR region. Preferably, the gene that promotes cell division does not encode a neural stimulant. Preferred genes to be expressed are vmyc, SV-40 T antigen, ras oncogene, polyoma large T antigen, neu oncogene or combinations thereof. Preferably, such proliferation-promoting genes and proteins are expressed or active in vitro but poorly expressed or inactive in vivo. The vmyc gene appears to be self-regulating in this manner. Alternatively, inducible promoters that require a factor, provided in vitro, to stimulate gene expression may be used.

Other Stem Cells

Certain embryonal tumors contain many multipotent cell types. In certain embodiments, cell lines established from these tumors may be used as part of a method for treating CNS injuries. Useful cell lines derived from embryonal tumors have been described. For example, cells of the NT2/Tera cell line are capable of differentiating into all of the major neural lineages (U.S. Pat. No. 5,175,103).

Such cells may be isolated from embryonal tumors by any of the general methods described above and in U.S. Pat. No. 5,175,103 and in Andrews (1984) *Dev. Biol.* 103: 285–293. In brief, a human teratocarcinoma cell line (Ntera 2/Cl.DI or NT2 cells) can be grown on retinoic acid to form a dense, multi-layered culture. These dense cultures are replated. Small, dense NT2-N cells are loosely associated with an underlying layer of cells. These can be easily dislodged and enriched, yielding a culture of small, round phase bright cells with some flat contaminating cells. NT2-N cells can be further enriched by culturing with a combination of mitotic inhibitors, such as cytosine arabinoside. The desired round cells are resistant to this treatment, while the flat cells do not proliferate. Enrichment of NT2-N cells tending towards a neural developmental pathway stain with an anti-NF-L antibody (low molecular weight neurofilament protein), while undifferentiated NT2 cells (flat cells) stain with Cam5.2 which reacts with keratins 8 and 18.

Non-cancerous embryonic tissue is also a source for stem cells. Early embryonic cells are totipotent, being capable of giving rise to the entire adult organism. As a result, such cells may be cultured to give totipotent or highly multipotent stem cells. Embryonic stem cells may be used as part of an inventive method for treating CNS injuries. Depending on culture conditions, these cells may eventually give rise to more committed cell types and certain terminally differentiated cell types. Embryonic stem cells may be obtained and cultured as described in Thomson et al. (1998) *Science* 282:1145–1147; Evans et al. (1981) *Nature* 292:154; Martin, G. (1981) *Proc. Natl. Acad. Sci. USA* 78:7634.

4.5 Administration

Administration of cells and other treatments may be carried out by various methods, and the methods need not be the same for each component. Generally, when the treatment is a chemical compound, the molecule can be administered by any known route of administration, including intravenously, orally, or intracerebrally (e.g., intraventricularly, intrathecally, or intracisternally, or directly into the brain). The dose may vary depending on the method of administration (see Table 2). Doses determined in rats are typically scaled up for human treatments. The scaling to be used depends upon the method of delivery. If the stimulant is to be delivered systemically (eg. orally or intravenously) then the scaling is by body weight, where a typical rat weighs 300 grams and a typical human weighs 70 kg. If the compound is to be delivered to the cerebrospinal fluid (eg. intracisternal, intraventricular), scaling is by brain surface area. A typical rat brain has a surface area of 1 cm$^2$, and a typical human brain has a surface area of 1000–10,000 cm$^2$, depending upon whether all of the various folds buried in convolutions are counted or not. If the compound is to be delivered to the brain tissue, scaling is done by brain mass. A typical rat has a 2 g brain, while the typical human brain is 2 kg. Thus, if a single treatment of 0.5 μg given intracisternally is effective in a rat, it would be expected that an intracisternal injection of 0.5 mg would be effective in a human patient. Of course exact dosages can be adjusted according to the weight of the patient and other criteria. It is anticipated that effective dosage for all three general routes of administration may range from 0.001–1000 mg total for administration to spinal fluid or brain tissue. In preferred embodiments, the dosage may range from 0.01–100 mg, 0.1–10 mg or 0.5–5 mg.

TABLE 2

Scaling for dosages of cells and stimulants

| | Method of Administration | | |
|---|---|---|---|
| Subject | Systemic (scale by body weight) | To Spinal Fluid (scale by brain surface area) | To Brain Tissue (scale by brain weight) |
| Rat | 300 grams | 1 $cm^2$ | 2 grams |
| Human | 70 kg | 1000–10,000 $cm^2$ | 2 kg |

Compounds may be administered in a single dose or they may be distributed in a series of smaller doses. For example, intracisternal administration can consist of a single injection given, for example, six hours after an injury, a pair of injections, given, for example, 24 and 48 hours after an injury, or, if necessary, a series of injections of, for example, 0.1 mg/injection, or a 1 mg injection, given biweekly (for example, every 34 days) in a treatment regimen that occurs at least six hours following the ischemic episode. The treatment regimen may last a number of weeks.

In certain embodiments, the cells are preferably administered directly into the stroke cavity, the spinal fluid, e.g., intraventricularly, intrathecally, or intracisternally. The cells are carried in a pharmaceutically acceptable liquid medium, which can contain the bioactive molecule as well. As an alternative, the cells (alone or mixed with the stimulant) can be administered to the stroke cavity or into the spinal fluid bathing the brain (e.g., intrathecal or intracisternal administration). Cells may also be injected into the region of the brain surrounding the area(s) of damage, and cells may be given systemically, given the ability of certain stem cells to migrate to the appropriate position in the brain. If the cells are to be injected into the stroke cavity, the ventricles of the brain, or into the brain tissue, the patient's head is immobilized in a standard stereotactic frame, and the site of administration of the cells is located by standard CT or MRI scan. A small-bore hole is drilled in the skull, and the cells are injected into the desired location using a syringe. Cells are scaled according to method of administration as detailed in table 2. Generally, between $10^6$ and $10^{12}$ cells are administered in total, preferably between $10^7$ and $10^{11}$ and more preferably between $10^8$ and $10^{10}$. Multiple cell administrations can be used, generally at least 2–7 days apart.

Administration of cells and treatments will be preferably carried out anywhere from several hours or several days following the injury to several weeks or even months following the stroke. In preferred embodiments, administration is carried out at least 6, 10, 12 or 24 hours after the injury has occurred. It is anticipated that exact dosages for both cells and neural stimulants may be adjusted by the medical practitioner in response to the particular needs and characteristics of the patient. In general it is expected that the optimal dosage is high enough to be effective but low enough to avoid provoking excessive inflammatory response, which can be counter-productive. By determining the level of inflammatory response, one could determine whether a particular dosage rate is too high to give optimal effectiveness. The methods of administration presented herein are preferred because they permit precise control and modulation of dose levels and because the area to which cells and stimulants are applied can be carefully controlled. In preferred embodiments, the neural stimulant is not produced from a transgene contained within one or more of the administered cells.

Other desirable compounds may be administered with the cells and neural stimulants. For example, immunosuppressants and antibiotics are useful for preventing graft rejection and infection, respectively. Furthermore, as discussed above, these types of compounds may have additional beneficial effects.

Common methods of administering the cells and bioactive factors of the present invention to subjects, particularly human subjects, which are described in detail herein, include injection or implantation of the cells and/or neural stimulants into target sites in the subjects. The cells and factors of the invention can be inserted into a delivery device which facilitates introduction by injection or implantation into the subjects. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The cells and factors of the invention can be inserted into such a delivery device, e.g., a syringe, in different forms. For example, the cells or factors can be suspended in a solution or embedded in a support matrix when contained in such a delivery device. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating progenitor cells as described herein in a pharmaceutically acceptable carrier or diluent and, as required, other ingredients enumerated above, followed by filtered sterilization.

Optionally, cells may be administered on support matrices. Support matrices in which cells can be incorporated or embedded include matrices which are recipient-compatible and which degrade into products which are not harmful to the recipient. Natural and/or synthetic biodegradable matrices are examples of such matrices. Natural biodegradable matrices include plasma clots, e.g., derived from a mammal, and collagen matrices. Synthetic biodegradable matrices include synthetic polymers such as polyanhydrides, polyorthoesters, and polylactic acid. Other examples of synthetic polymers and methods of incorporating or embedding cells into these matrices are known in the art. See e.g., U.S. Pat. No. 4,298,002 and U.S. Pat. No. 5,308,701. These matrices provide support and protection for the cells in vivo.

Cells and neural stimulants of the invention may be administered together in a pharmaceutical composition. Appropriate compositions may include all compositions usually employed for systemically or locally administering drugs. The pharmaceutically acceptable carrier should be substantially inert, so as not to act with the active components or interfere with cell viability. Suitable inert carriers include water, alcohol polyethylene glycol, propylene glycol and the like.

To prepare the pharmaceutical compositions of this invention, an effective amount of the particular neural stimulant and cells as active ingredients are combined with a pharmaceutically acceptable carrier, which carrier may take a wide variety of forms depending on the form of preparation desired for administration. These pharmaceutical compositions are desirable in unitary dosage form suitable, particularly, for administration percutaneously, or by parenteral injection. Any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. For parenteral compositions, the carrier will usually comprise sterile water, at least in large part, though other ingredients, for example, to aid solubility and cell viability, may be included. Other ingredients may include antioxidants, viscosity stabilizers, chelating agents, buffers, preservatives. If desired, further ingredients may be incorporated in the compositions, e.g. anti-inflammatory agents, antibacterials, antifungals, disinfectants, vitamins, antibiotics.

Examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

It is especially advantageous to formulate the subject compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are capsules, injectable solutions or suspensions, teaspoonfuls, tablespoonfuls and the like, and segregated multiples thereof.

Particular compositions for use in the method of the present invention are those wherein the neural stimulant is formulated in liposome-containing compositions. Liposomes are artificial vesicles formed by amphiphatic molecules such as polar lipids, for example, phosphatidyl cholines, ethanolamines and serines, sphingomyelins, cardiolipins, plasmalogens, phosphatidic acids and cerebrosides. Liposomes are formed when suitable amphipathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamnellar vesicle. If water-soluble materials are included in the aqueous phase during the swelling of the lipids they become entrapped in the aqueous layer between the lipid bilayers.

Water-soluble active ingredients are encapsulated in the aqueous spaces between the molecular layers. A lipid soluble active ingredient of a neural stimulant, such as an organic mimetic, is predominantly incorporated into the lipid layers, although polar head groups may protrude from the layer into the aqueous space. The encapsulation of these compounds can be achieved by a number of methods. The method most commonly used involves casting a thin film of phospholipid onto the walls of a flask by evaporation from an organic solvent. When this film is dispersed in a suitable aqueous medium, multilamellar liposomes are formed. Upon suitable sonication, the coarse liposomes form smaller similarly closed vesicles.

Water-soluble active ingredients are usually incorporated by dispersing the cast film with an aqueous solution of the compound. The unencapsulated compound is then removed by centrifugation, chromatography, dialysis or other artknown suitable procedures. The lipid-soluble active ingredient is usually incorporated by dissolving it in the organic solvent with the phospholipid prior to casting the film. If the solubility of the material in the lipid phase is not exceeded or the amount present is not in excess of that which can be bound to the lipid, liposomes prepared by the above method usually contain most of the material bound in the lipid bilayers; separation of the liposomes from unencapsulated material is not required.

A particularly convenient method for preparing liposome formulated forms of neural stimulants is the method described in EP-A-253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously.

The single bilayered liposomes containing the encapsulated neural stimulant can be mixed with cells and then employed directly or they can be employed in a suitable pharmaceutically acceptable carrier for localized administration. The viscosity of the liposomes can be increased by the addition of one or more suitable thickening agents such as, for example xanthan gum, hydroxypropyl cellulose, hydroxypropyl methylcellulose and mixtures thereof The aqueous component may consist of water alone or it may contain electrolytes, buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatidylserine, phosphatidylethanol-amine, phosphatidylinositol, lysophosphatidylcholine and phosphatidyl glycerol, for example. Other lipophilic additives may be employed in order to selectively modify the characteristics of the liposomes. Examples of such other additives include stearylamine, phosphatidic acid, tocopherol, cholesterol and lanolin extracts.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such a benzoic acid, methyl paraben and propyl paraben may also be added.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a bioactive factor at a particular target site.

An essential feature of certain embodiments of the implant can be the linear release of the therapeutic, which can be achieved through the manipulation of the polymer composition and form. By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, *Concise Encyclopedia of Medical & Dental Materials*, ed. by David Williams (MIT Press: Cambridge, Mass., 1990); and the Sabel et al. U.S. Pat. No. 4,883,666.

In another embodiment of an implant cells are encapsulated in implantable hollow fibers or the like. Such fibers can be pre-spun and subsequently loaded with the cell source (Aebischer et al. U.S. Pat. No. 4,892,538; Aebischer et al. U.S. Pat. No. 5,106,627; Hoffman et al. (1990) *Expt. Neurobiol.* 110:39–44; Jaeger et al. (1990) *Prog. Brain Res.* 82:41–46; and Aebischer et al. (1991) *J. Biomech. Eng.* 113:178–183), or can be co-extruded with a polymer which acts to form a polymeric coat about the cells (Lim U.S. Pat. No. 4,391,909; Sefton U.S. Pat. No. 4,353,888; Sugamori et al. (1989) *Trans. Am. Artif. Intern. Organs* 35:791–799; Sefton et al. (1987) *Biotehnol. Bioeng.* 29:1135–1143; and Aebischer et al. (1991) *Biomaterials* 12:50–55). Such encapsulated cells can then be combined with a neural stimulant.

It is anticipated that, for convenience, it would be desirable for neural stimulants and cells to be packaged together into kits. Kits may include dose-size-specific ampules or aliquots of cells and/or neural stimulants. Kits may also contain devices to be used in administering the components of the conjoint administration. Such devices have been described above. In certain embodiments, wherein the cells are to be obtained from the patient, cultured, and readministered to the patient, the kit may comprise a device for obtaining a cell sample from the patient from which stem cells will be cultured.

In certain aspects, practitioners of the present invention may employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

The invention now being generally described, it will be more readily understood by reference to the following examples which are included merely for purposes of illustration of certain aspects and embodiments of the present invention, and are not intended to limit the invention.

5. EXAMPLES

Example 1

Intracisternal Neural Stem Cells (NSC) and Growth Factors Enhance Stroke Recovery In this example, fetal mouse neural stem cells (NSC) with or without basic fibroblast growth factor (bFGF) were administered intracisternally in a model of stroke recovery in rats. Male Sprague-Dawley rats, 300–350 grams, were handled for one week before surgery. They received an antibiotic, cefazolin sodium (40 mg/kg, i.p.), one day before stroke surgery. On the day of stroke surgery, animals were anesthetized by 2% halothane in a nitric oxide/oxygen mixture (2:1). Focal cerebral infarction, (stroke) was performed by proximal electrocoagulation of the middle cerebral artery, as described previously (Kawamata et al. (1999) *Exp. Neurol.* 158, 89–96; Tamura et al. (1981) *J. Cereb. Blood Flow Metab.* 1, 53–60). Specifically, the artery was occluded from just proximal to the olfactory tract to the inferior cerebral vein, without removing the zygomatic arch or transsection of the facial nerve. This technique produces a robust and reproducible infarct, or region of cell death, in the dorsolateral cerebral cortex and underlying striatum. Animals received another injection of cefazolin sodium (40 mg/kg, i.p.) immediately after surgery. They were then allowed to awaken from anesthesia.

Twenty-four hours after stroke surgery, animals received an intracisternal injection of either: (1) vehicle, (2) NSC ($10^6$ cells), (3) bFGF (0.5 $\mu$g), or (4) NSC+bFGF. Intracisternal injection in 50 $\mu$l total volume was done through percutaneous injection into the cisterna magna under halothane anesthesia. This same procedure was repeated two days later so that animals received treatment on days 1 and 3 following stroke. Cyclosporin, an immunosuppressant, was administered at 10 mg/kg, i.p. for the duration of the experiment.

The cerebral infarcts produced by the procedure cause sensorimotor dysfunction of the contralateral hindlimb and forelimb. For the next month following stroke, a number of neurological tests were done to assess sensorimotor function of the contralateral limbs. These tests include both the forelimb and hindlimb placing tests which test the animal's ability to place the limb on a tabletop in response to visual, tactile, proprioceptive, and whisker stimulation. In addition, a body swing test was done that measures the side to side preferences of the animal as he is held suspended by his tail above a tabletop. Finally, the spontaneous limb use test is done which measures the animal's propensity to use each forelimb spontaneously as he rears up to explore the inside of a narrow glass cylinder. The forelimb and hindlimb placing test, as well as the spontaneous limb use test reflect both cortical and striatal function. The body swing test is mainly a measure of striatal function.

The results of these tests are shown in FIGS. 1A–1D. Panels (A) and (B) show placing activity of the affected forelimb and hindlimb (contralateral to the side of the stroke in the brain). Panel (C) shows the body swing test, and panel (D) shows the spontaneous limb use test. In each instance, normal behavior is indicated by the data obtained on the day before surgery (−1 day). In each case, animals showed markedly abnormal behavior on the day following surgery. There was then a slow spontaneous recovery that was incomplete. FIGS. 1A–1D show that on the limb placing tests all three treatments: NSC, bFGF and the combination, significantly enhanced recovery compared to placebo. There was a similar trend in the spontaneous limb use test. No differences among treatments compared to placebo were seen on the body swing test. In addition, although this was nonsignificant, a trend toward superior enhancement of function was seen in the combination group compared to the NSC and bFGF groups alone.

At one month following stroke, animals were sacrificed, brains were removed and sectioned and stained with H & E. Infarct volume was determined via image analysis, as described previously (Kawamata et al. (1996) *J. Cereb. Blood Flow Metab.* 16, 542–547; Kawamata et al. (1997) *Proc. Nat. Acad. Sci.* 94, 8179–8184). No significant differences were seen in infarct volume among groups, although there was a trend toward slightly smaller infarct volume in the groups receiving NSC. The stem cells that were transplanted contain the lacZ reporter gene and express β-galactosidase. X-gal histochemistry was done to examine the location of these cells post-transplant. Indeed, the cells had migrated from their site of installation in the cisterna magna to positions surrounding the focal stroke in the right hemisphere.

In summary, this experiment showed that NSC and/or bFGF administered intracisternally starting one day after stroke can significantly enhance sensorimotor recovery of the contralateral limbs. This improvement was largely confined to tests reflecting cortical function. No significant differences were seen in infarct volume among the groups, suggesting that NSC and bFGF produced recovery-promoting effects through other mechanisms than the prevention of cell death. These mechanisms may include establishing new connections in undamaged parts of brain. Moreover in this first experiment, the combination of NSC and bFGF appeared to be slightly superior to either treatment alone.

Example 2

Direct Intracerebral Administration of NSC and Intracisternal Administration of bFGF Enhance Recovery in Rat Stroke Model In a second experiment, NSC were injected directly into the brain into tissue surrounding focal strokes. bFGF was injected intracisternally, as before. In this experiment only one administration of NSC or bFGF was performed at one day after stroke. Under these conditions, we clearly observed the superiority of NSC+bFGF compared to either treatment alone.

In this experiment, animals were handled for one week before surgery. In addition, they were trained on an additional test, the paw reaching test (see below) for 10 days before surgery. As before, they received cefazolin sodium (40 mg/kg, i.p.) before surgery. On the day of surgery, electrocoagulation of the proximal middle cerebral artery was done, as described previously (Kawamata et al. (1996) *J. Cereb. Blood Flow Metab.* 16, 542–547; Kawamata et al. (1997) *Proc. Nat. Acad Sci.* 94, 8179–8184; Kawamata et al. (1999) *Exp. Neurol.* 158, 89–96). They received another injection of cefazolin sodium, 40 mg/kg, i.p. after surgery.

At one day after stroke, animals received either: (1) vehicle injection into periinfarct tissue, and vehicle injection into the cisterna magna, (2) NSC ($10^6$ cells) into periinfarct tissue and vehicle into the cisterna magna, (3) vehicle into periinfarct tissue and bFGF (0.5 $\mu$g) into the cisterna magna or (4) the combination NSC ($10^6$ cells) into periinfarct tissue and bFGF (0.5 $\mu$g) into the cisterna magna.

These injections were done with a volume of 25 $\mu$l each under 2% halothane anesthesia. NSC was injected into striatal tissue at the margins of focal infarcts. bFGF was injected percutaneously into the cisterna magna (intracisternal injection) as described previously (Kawamata et al. (1996) *J. Cereb. Blood Flow Metab.* 16, 542–547; Kawamata et al. (1997) *Proc. Nat. Acad. Sci.* 94, 8179–8184; Kawamata et al. (1999) *Exp. Neurol.* 158, 89–96). Rats also received cyclosporin, an immunosuppressant (10 mg/kg, i.p. per day), throughout the duration of the experiment.

As before, a number of behavioral tests were done for the next month following stroke. These tests included the forelimb and hindlimb placing tests, the body swing test, and the spontaneous limb use test, as described in Example 1. In addition, another test was done, the paw reaching test. Animals were trained on this test before stroke surgery, and then were tested once at the end of the experiment. This test examines the animal's ability to reach through the bars of his cage to grab and eat food pellets with the impaired (contralateral) forepaw. Normally, animals have about 100% accuracy in performing this task. Following stroke, it drops down to about 10%.

The results of these behavioral tests are shown in FIGS. 2A–2D and 3. Again, all three treated groups: NSC, bFGF, and the combination of NSC+bFGF, showed superiority in recovery on the forelimb and hindlimb placing tests compared to placebo. Again, there was a trend towards best recovery in the combination group. In the body swing test, NSC treatment alone did not show advantage over placebo, but both the bFGF and combination groups did. In the spontaneous limb use test, only the combination group showed a trend toward improved outcome. Finally, in the paw reaching test, the combination group appeared to show superiority compared to either treatment alone. Histological evaluation of these brains is still pending.

In summary, in this experiment NSC was injected directly into tissue bordering focal strokes. bFGF was administered intracisternally. Each of these treatments, when delivered alone, improved behavioral outcome on some tests. For each test, the combination treatment appeared to be better than either treatment alone. This was particularly apparent on the spontaneous limb use and paw reaching tests. This experiment supports the notion that the combination of stem cell and growth factor treatment is superior to either treatment alone in enhancing stroke recovery. Both of the examples above were done using only one dose of NSC and growth factor. Further studies are underway to define the dose response characteristics of this interaction.

Equivalents

Those skilled in the art will recognize, or be able to ascertain using no more than routine experimentation, many equivalents to the specific embodiments of the invention described herein. Such equivalents are intended to be encompassed by the following claims.

---

What is claimed is:

1. A method of treating a subject with CNS ischemic damage, said method comprising administering to said subject:

hematopoietic stem cells; and a fibroblast growth factor (FGF);

wherein the conjoint administration of the hematopoietic stem cells and the FGF ameliorates effects of CNS ischemic damage.

2. The method of claim 1, wherein the FGF is a basic fibroblast growth factor.

3. The method of claim 1, wherein the hematopoietic stem cells are obtained from fetal blood.

4. The method of claim 1, wherein the hematopoietic stem cells are administered intravenously, intracerebrally, intraventricularly or intracisternally.

5. The method of claim 1, wherein the hematopoietic stem cells and the FGF are both administered intravenously.

6. A method of treating a subject with brain damage resulting from stroke, said method comprising administering to said subject:

hematopoietic stem cells; and a fibroblast growth factor (FGF);

wherein the conjoint treatment with the hematopoietic stem cells and the FGF ameliorates effects of brain damage.

7. The method of claim 6, wherein said conjoint treatment is initiated at least 6 hours after the stroke was diagnosed.

* * * * *

UNITED STATES PATENT AND TRADEMARK OFFICE
CERTIFICATE OF CORRECTION

PATENT NO. : 6,749,850 B1
DATED : June 15, 2004
INVENTOR(S) : Finkelstein et al.

It is certified that error appears in the above-identified patent and that said Letters Patent is hereby corrected as shown below:

Column 2,
Lines 47 and 52, replace "neurotrarsmitters" with -- neurotransmitters --.

Column 3,
Line 24, replace "identica" with -- identical --; and
Line 64, replace "neurotrarsmitter" with -- neurotransmitter --.

Column 23,
Line 30, replace "34 days" with -- 3-4 days --.

Column 26,
Line 7, replace "unilamnellar" with -- unilamellar --.

Column 27,
Line 12, replace "phosphatidylethanol-amine" with -- phosphatidylethanolamine --.

Signed and Sealed this

Fourth Day of October, 2005

JON W. DUDAS
*Director of the United States Patent and Trademark Office*